United States Patent
Kornbluth et al.

(10) Patent No.: US 9,937,178 B2
(45) Date of Patent: Apr. 10, 2018

(54) METHODS OF IDENTIFYING AND USING MDM2 INHIBITORS

(71) Applicant: DUKE UNIVERSITY, Durham, NC (US)

(72) Inventors: Sally Kornbluth, Durham, NC (US); Manabu Kurokawa, Durham, NC (US); Neil Spector, Durham, NC (US); Mark Dewhirst, Durham, NC (US)

(73) Assignee: Duke University, Durham, NC (US)

( * ) Notice: Subject to any disclaimer, the term of this patent is extended or adjusted under 35 U.S.C. 154(b) by 345 days.

(21) Appl. No.: 14/363,346

(22) PCT Filed: Dec. 7, 2012

(86) PCT No.: PCT/US2012/068557
§ 371 (c)(1),
(2) Date: Jun. 6, 2014

(87) PCT Pub. No.: WO2013/101436
PCT Pub. Date: Jul. 4, 2013

(65) Prior Publication Data
US 2014/0336202 A1 Nov. 13, 2014

Related U.S. Application Data

(60) Provisional application No. 61/567,944, filed on Dec. 7, 2011.

(51) Int. Cl.
| | |
|---|---|
| *A61K 31/517* | (2006.01) |
| *G01N 33/50* | (2006.01) |
| *A61K 39/395* | (2006.01) |
| *C07K 16/32* | (2006.01) |
| *C12N 15/113* | (2010.01) |
| *A61K 45/06* | (2006.01) |
| *A61K 31/496* | (2006.01) |
| *A61K 31/404* | (2006.01) |
| *A61K 31/407* | (2006.01) |

(52) U.S. Cl.
CPC .......... *A61K 31/517* (2013.01); *A61K 31/404* (2013.01); *A61K 31/407* (2013.01); *A61K 31/496* (2013.01); *A61K 39/39558* (2013.01); *A61K 45/06* (2013.01); *C07K 16/32* (2013.01); *C12N 15/1135* (2013.01); *C12N 15/1137* (2013.01); *C12Y 603/02* (2013.01); *G01N 33/5011* (2013.01); *C12N 2310/14* (2013.01); *C12N 2310/531* (2013.01); *G01N 2800/52* (2013.01)

(58) Field of Classification Search
CPC ............ A61K 31/517; A61K 39/39558; A61K 45/06; A61K 31/496; A61K 31/404; A61K 31/407; G01N 33/5011; G01N 2800/52; C07K 16/32; C12Y 603/02; C12N 15/1135; C12N 15/1137; C12N 2310/14; C12N 2310/531

See application file for complete search history.

(56) References Cited

U.S. PATENT DOCUMENTS

2011/0112052 A1  5/2011  Wang et al.

FOREIGN PATENT DOCUMENTS

| WO | WO 2003/051360 | 6/2003 |
| WO | WO 2012/012653 | 1/2012 |

OTHER PUBLICATIONS

Martin et al., Inhibition of MCL-1 enhances lapatinib toxicity and overcomes lapatinib resistance via BAK-dependent autophagy. Cancer Biol. Ther. 8:2084-2096, 2009.*
Morel, C. et al., "Mcl-1 Integrates the Opposing Actions of Signaling Pathways that Mediate Survival and Apoptosis," Molecular and Cellular Biology (2009) 29(14):3845-3852.
Nijhawan, D. et al., "Elimination of Mcl-1 is required for the initiation of apoptosis following ultraviolet irradiation," Genes & Development (2003) 17:1475-1486.
Ohnstad, H.O. et al., "MDM2 antagonist Nutlin-3a potentiates antitumour activity of cytotoxic drugs in sarcoma cell lines," BMC Cancer (2011) 1-11.
Peirce, S. K. et al., "The MDM2 antagonist nutlin-3 sensitizes p53-null neuroblastoma cells to doxorubicin via E2F1 and TAp73," *International Journal of Oncology* 34(5):1395-1402 (2009).
Pepper, C. et al., "Mcl-1 expression has in vitro and in vivo significance in chronic lymphocytic leukemia and is associated with other poor prognostic markers," Blood (2008) 112(9):3807-3817.
Peterson, L.F. et al., "Enhanced cytotoxicity in chronic myeloid leukemia primitive progenitors by the combined action of imatinib and an HDM2-inhibitor," *Blood* 112(11):1-2 (Abstract).
Pishas, K.I. et al., "Nutlin-3a is a Potential Therapeutic for Ewing Sarcoma," Clin Cancer Res (2010) 17(3):494-504.

(Continued)

*Primary Examiner* — Ruixiang Li
(74) *Attorney, Agent, or Firm* — Andrus Intellectual Property Law, LLP

(57) ABSTRACT

Methods of treating subjects with cancer and screening for MDM2 inhibitors that may be effective cancer therapeutics are provided herein. The cancers that may be treated using MDM2 inhibitors using the methods described herein include those that are or may become resistant to treatment with tyrosine kinase inhibitors. Methods of treating subjects with cancers that have, or develop in response to treatment with tyrosine kinase inhibitors, elevated levels of MDM2, Mcl-1 or PP5 or decreased levels of Huwe1 or CAS using MDM2 inhibitors are provided herein. The MDM2 inhibitors may be effective at treating these cancers alone or in combination with a tyrosine kinase inhibitor regardless of p53 status (mutant or wild-type) of the cancer.

14 Claims, 18 Drawing Sheets

(56) References Cited

OTHER PUBLICATIONS

Rexer, B.N. et al., "Phosphoproteomic mass spectrometry profiling links Src family kinases to escape from HER2 tyrosine kinase inhibition," *Oncogene* 30(40):4163-74 (2011).
Saha, M.N. et al., "RITA Inhibits Multiple Myeloma Cell Growth through Induction of p53-Mediated Caspase-Dependent Apoptosis and Synergistically Enhances Nutlin-Induced Cytotoxic Responses," (2010) *Mol. Cancer Therapeutics* 9(11):3041-3051.
Secchiero, P. et al., "The MDM2 inhibitor nutlins as an innovative therapeutic tool for the treatment of haematological malignancies," *Current Pharmaceutical Design* 14(21):2100-2110 (2008).
Schwickart, M. et al., "Deubiquitinase USP9X stabilizes MCL1 and promotes tumour cell survival," Nature (2010) 463:103-108.
Shangary, S. et al., "Small-Molecule Inhibitors of the MDM2-p53 Protein-Protein Interaction to Reactivate p53 Function: A Novel Approach for Cancer Therapy," (2009) *Annu Rev Pharmacol Toxicol* 49:223-241.
Tanaka, T. et al., "hCAS/CSE1L associates with chromatin and regulates expression of select p53 target genes," *Cell* 130, 638-650 (2007).
Tovar, C. et al., "Small-molecule MDM2 antagonists reveal aberrant p53 signaling in cancer: Implications for therapy," PNAS 103(6):1888-1893.
Uesugi, M. et al. "The α-helical FXXΦΦ motif in p53: TAF interaction and discrimination by MDM2," *Proc. Natl. Acad. Sci. USA* 96, 14801-14806 (1999).
Vassilev, L.T. et al., "In vivo activation of the p53 pathway by small-molecule antagonists of MDM2," *Science* 303, 844-848 (2004).
Vrana, J.A. et al., "An MCL1-overexpressing burkitt lymphoma subline exhibits enhanced survival on exposure to serum deprivation, topoisomerase inhibitors, or staurosporine but remains sensitive to 1-Beta-D-Arabinofuranosylcytosine," Cancer Research (2002) 62:892-900.
Wade, M. et al., "Targeting Mdm2 and Mdmx in Cancer Therapy: Better Living through Medicinal Chemistry?" Mol Cancer Res (2009) 7(1):1-11.
Wandinger, S.K. et al., "The phosphatase Ppt1 is a dedicated regulator of the molecular chaperone Hsp90," *EMBO J.* 25, 367-376 (2006).
Wang, J. et al., "MDM2 antagonist can inhibit tumor growth in hepatocellular carcinoma with different types of p53 in vitro," *J. of Gastroenterology and Hepatology* 26(2):371-377 (2011).
Wertz, I.E. et al., "Sensitivity to antitubulin chemotherapeutics is regulated by MCL1 and FBW7," Nature (2011)471:110-114, 122.
Xia, W. et al. "A model of acquired autoresistance to a potent ErbB2 tyrosine kinase inhibitor and a therapeutic strategy to prevent its onset in breast cancer," *Proc. Natl. Acad. Sci. USA* 103(20):7795-7800 (2006).
Yang, Y. et al., "Small molecule inhibitors of HDM2 ubiquitin ligase activity stabilize and activate p53 in cells,"Cancer Cell (2005) 7:547-559.
Zhang, S. et al. "Combating trastuzumab resistance by targeting SRC, a common node downstream of multiple resistance pathways," *Nat. Med.* 17(4):461-469 (2011).
Zhang, W. et al., "Blockade of Mitogen-Activated Protein Kinase/Extracellular Signal-Regulated Kinase Kinase and Murine Double Minute Synergistically Induces Apoptosis in Acute Myeloid Leukemia via BH3-Only Proteins Puma and Bim," Cancer Research (2010) 70(6):2424-2434.
Zhong, Q. et al., "Mule/ARF-BP1, a BH3-Only E3 Ubiquitin Ligase, Catalyzes the Polyubiquitination of Mcl-1 and Regulates Apoptosis," Cell (2005) 121:1085-1095.
International Search Report and Written Opinion for PCT/US2012/068557 dated Apr. 22, 2013 (17 pages).
Partial Supplementary European Search Report for European Application No. 12861144.9 dated Jul. 30, 2015 (9 pages).
Extended European Search Report for European Application No. 12861144.9 dated Nov. 30, 2015 (21 pages).

Ambrosini, G. et al., "Mouse double minute antagonist Nutlin-3a enhances chemotherapy-induced apoptosis in cancer with mutant p53 by activating E2F1," *Oncogene* 26(24):3473-3481 (2007).
Barbieri, E. et al., "MDM2 inhibition sensitizes neuroblastoma to chemotherapy-induced apoptotic cell death," Mol Cancer Ther (2006) 5(9):2358-2365.
Bhattacharya, S. et al. "Mdm2 antagonist Nutlin-3 induces apoptosis in p53 mutant human colon carcinoma cells," *The FASEB Journal* 23(1):618-12 Meeting Abstracts (2009) (Abstract).
Bianco, R. et al., "Combined Targeting of Epidermal Growth Factor Receptor and MDM2 by Gefitinib and Antisense MDM2 Cooperatively Inhibit Hormone-Independent Prostate Cancer," *Clin. Cancer Res.* 10(14):4858-4864.
Bozzi, F. et al., "In vitro and in silico studies of MDM2/MDMX isoforms predict Nutlin-3A sensitivity in well/de-differentiated liposarcomas," Laboratory Investigation (2013) 93:1232-1240.
Cohen, P. et al., "Will the Ubiquitin System Furnish as Many Drug Targets as Protein Kinases?" Cell (2010) 143:686-693.
Cuconati, A. et al., "DNA damage response and MCL-1 destruction initiate apoptosis in adenovirus-infected cells," Genes & Development (2003) 17:2922-2932.
Ding, Q. et al., "Degradation of Mcl-1 η -TrCP Mediates Glycogen Synthase Kinase 3-Induced Tumor Suppression and Chemosensitization," Molecular and Cellular Biology, Jun. 2007, 4006-4017.
Graat, H. C. A. et al., "Enhanced tumor cell kill by combined treatment with a small-molecule antagonist of mouse double minute 2 and adenoviruses encoding p53," *Molecular Cancer Therapeutics* 6(5):1552-1561 (2007).
Harley, M.E. et al., "Phosphorylation of Mcl-1 by CDK1—cyclin B1 initiates its Cdc20-dependent destruction during mitotic arrest," The EMBO Journal (2010) 29:2407-2420.
Inuzuka, H. et al., "Mcl-1 Ubiquitination and Destruction," Oncotarget (2011) 2:239-244.
Inuzuka, H. et al., "SCFFBW7 regulates cellular apoptosis by targeting MCL1 for ubiquitylation and destruction," Nature (2011) 471:104-111.
Jones, et al "Inhibition of the P53 E3 ligase HDM-2 induces apoptosis and DNA damage—independent p53 phosphorylation in mantle cell lymphoma," (2008) *Clin. Cancer Res.* 14(17):5416-5425.
Kim, H.-E. et al., "PHAPI, CAS, and Hsp70 promote apoptosome formation by preventing Apaf-1 aggregation and enhancing nucleotide exchange on Apaf-1," *Mol. Cell* 30, 239-247 (2008).
Kojima, K. et al., "Selective FLT3 inhibitor FI-700 neutralizes Mcl-1 and enhances p53-mediated apoptosis in AML cells with activating mutations of FLT3 through Mcl-1/Noxa axis," (2010) *Leukemia* 24(1):33-43.
Kojima, K. et al., "p53 activation of mesenchymal stromal cells partially abrogates microenvironment-mediated resistance to FLT3 inhibition in AML through HIF-1α-mediated down-regulation of CXCL12," *Blood* 118(16):4431-4439 (2011).
Kurokawa, M. et al., "Inhibition of apoptosome formation by suppression of Hsp90beta phosphorylation in tyrosine kinase-induced leukemias," *Mol. Cell. Biol.* 28, 5494-5506 (2008).
Kurokawa, M. et al., "A network of substrates of the E3 ubiquitin ligases MDM2 and HUWE1 control apoptosis independently of p53," *Sci Signal.* May 7, 2013;6(274).
Kurosu, T. et al., "Enhancement of imatinib-induced apoptosis of BCR/ABL-expressing cells by nutlin-3 through synergistic activation of the mitochondrial apoptotic pathway," (2010) *Apoptosis* 15(5):608-20.
Liu, H. et al., "Stabilization and Enhancement of the Antiapoptotic Activity of Mcl-1 by TCTP," Molecular and Cellular Biology, (2005), 25(8):3117-3126.
Long, J. et al., "Multiple distinct molecular mechanisms influence sensitivity and resistance to MDM2 inhibitors in adult acute myelogenous leukemia," Blood (2010) 116(1):71-80.
Manfredi, J.J., "The Mdm2—p53 relationship evolves: Mdm2 swings both ways as an oncogene and a tumor suppressor," (2010) *Genes Dev.* 24(15):1580-1589.

(56) References Cited

OTHER PUBLICATIONS

Maurer, U. et al., "Glycogen Synthase Kinase-3 Regulates Mitochondrial Outer Membrane Permeabilization and Apoptosis by Destabilization of MCL-1," Molecular Cell (2006) 21:749-760.
Mills, J.R. et al., "mTORC1 promotes survival through translational control of Mcl-1," PNAS (2008) 105(31):10853-10858.

* cited by examiner $^{35}$S-Mcl1

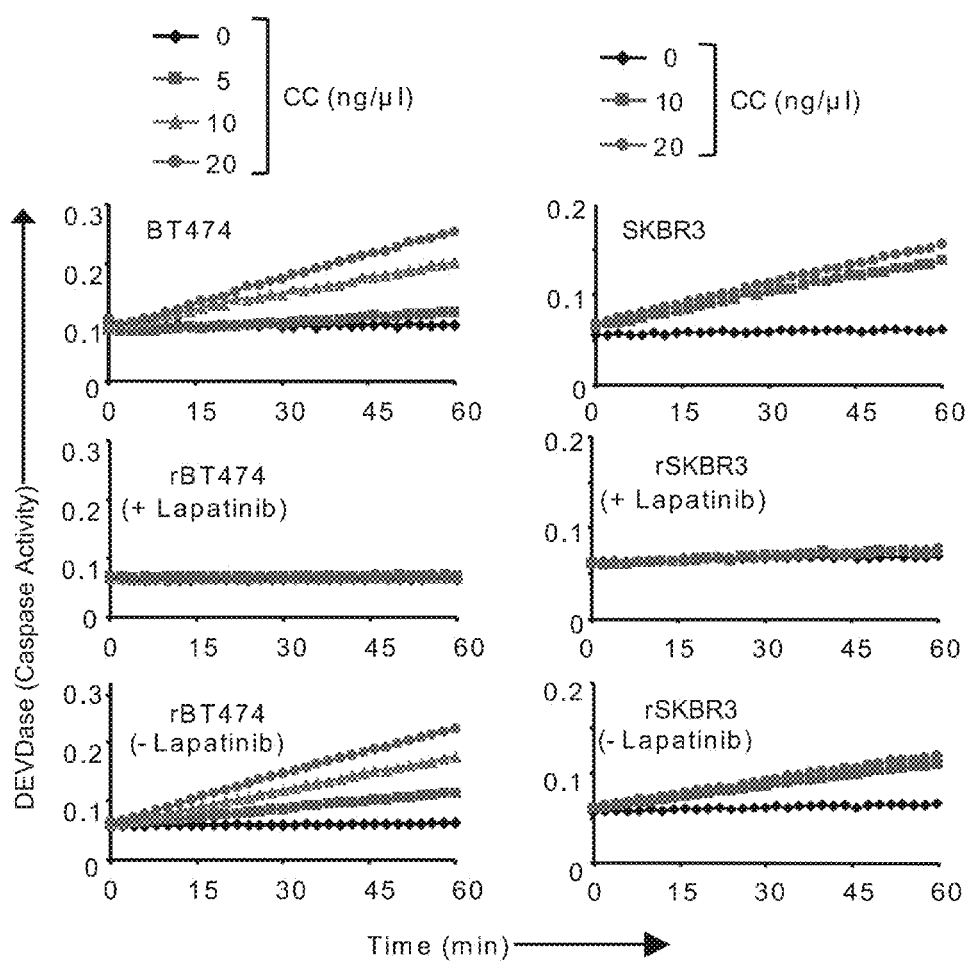

p-Ser226 p-Ser255

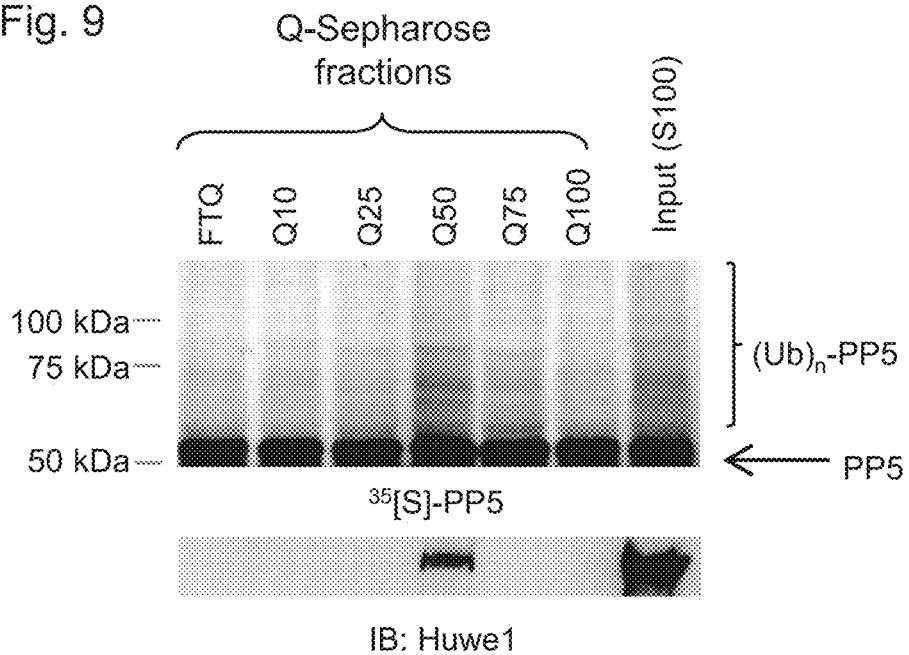
Fig. 9
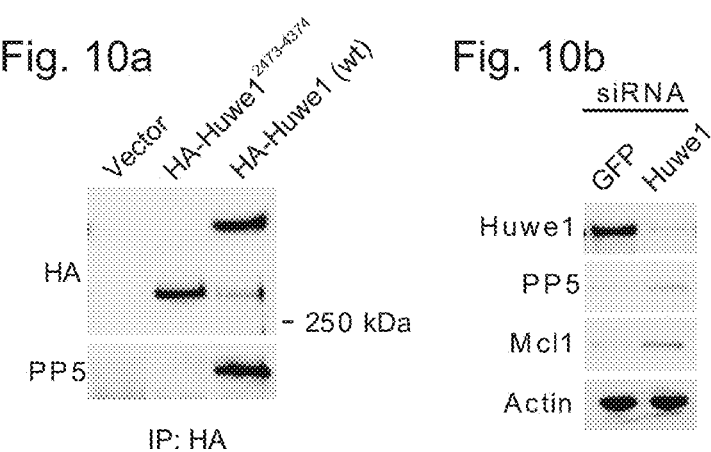
Fig. 10a
Fig. 10b
Fig. 10c
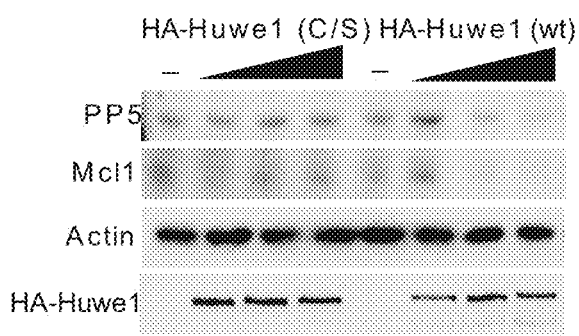

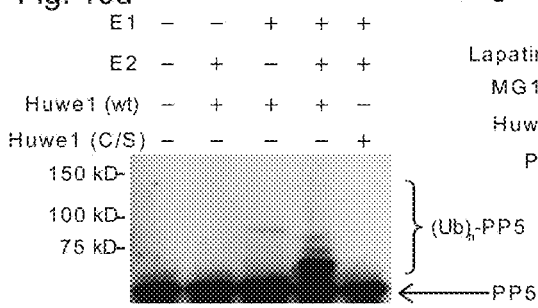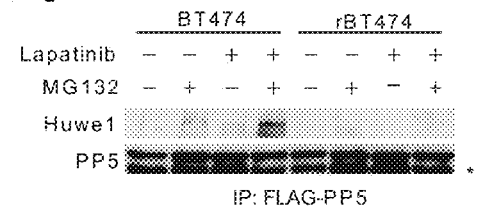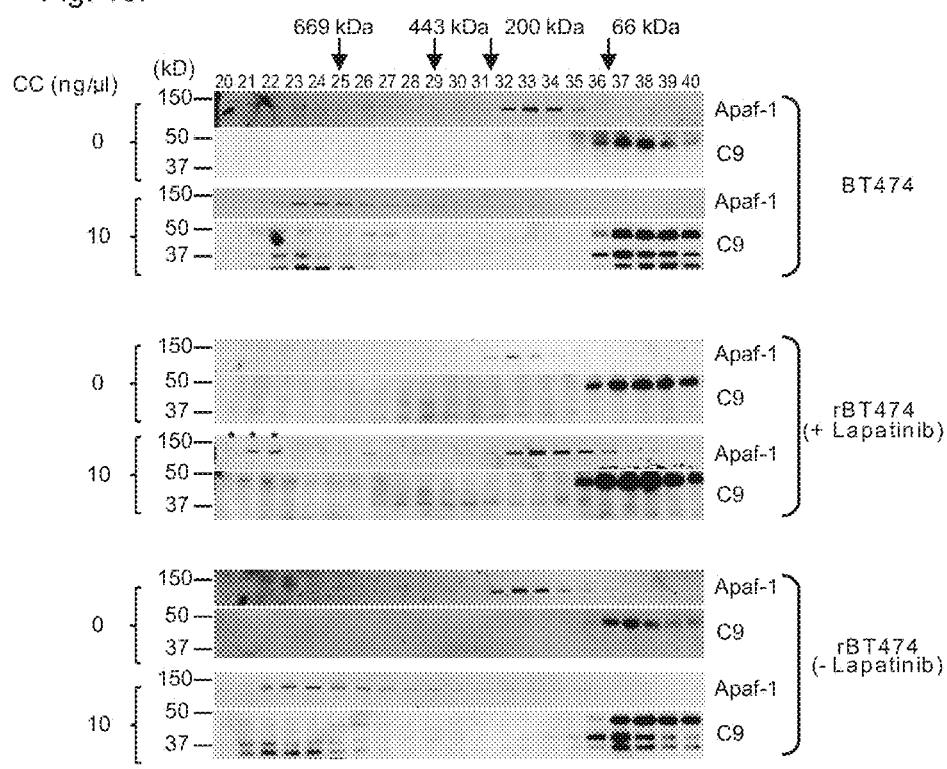

METHODS OF IDENTIFYING AND USING MDM2 INHIBITORS

STATEMENT REGARDING FEDERALLY SPONSORED RESEARCH

This invention was made with United States government support awarded by the National Institutes of Health grant number RO1 CA102707 and K99 CA140948. The United States may have certain rights in this invention.

CROSS-REFERENCE TO RELATED APPLICATIONS

This patent application is a national stage filing under 35 U.S.C. 371 of International Application No. PCT/US2012/068557, filed Dec. 7, 2012, which claims the benefit of priority of U.S. Provisional Patent Application No. 61/567,944, filed Dec. 7, 2011, both of which are incorporated herein by reference in their entirety.

SEQUENCE LISTING

A Sequence Listing accompanies this application and is incorporated herein by reference in its entirety. The Sequence Listing was filed with the application as a text file.

INTRODUCTION

In a subset of cancers, tumorigenesis is driven by activated tyrosine kinases that promote pro-survival/anti-apoptotic signaling. In these tumors, targeted kinase inhibition triggers apoptosis and tumor regression. However, acquired resistance to these inhibitors is a significant clinical problem. This resistance often results from mutations in the tyrosine kinase itself (e.g., imatinib-resistance stemming from mutation of Bcr-Abl in chronic myelogenous leukemias), but this is not always the case.

Overexpression of HER2 kinase in 20-30% of breast cancers is associated with poor clinical outcomes. Several HER2-directed therapeutics have been approved or are in clinical trials, including trastuzumab (Herceptin), a monoclonal antibody directed against the extracellular domain of HER2 kinase and lapatinib (Tykerb), a small molecule able to inhibit HER2 and EGFR kinase activities. Typically, a breast cancer patient undergoes lapatinib treatment after progressing on trastuzumab. However, the anti-tumor effects of lapatinib mono-therapy are generally short-lived, with cancer cells developing resistance to this drug over time.

Mechanisms underlying acquired lapatinib resistance are poorly understood particularly because mutations within HER2 itself are not typically seen in acquired lapatinib resistance. Several studies have identified apoptotic inhibitors whose expression levels are specifically upregulated in lapatinib resistant cells, including X-linked inhibitor of apoptosis protein (XIAP), and Mcl-1, an anti-apoptotic Bcl-2 family member (seen in lapatinib-resistant colon cancer cells).

SUMMARY

Provided herein are methods of treating subjects with cancer and screening for MDM2 inhibitors that may be effective cancer therapeutics. The cancers that may be treated using the methods described herein include those that are or may become resistant to treatment with tyrosine kinase inhibitors or have elevated levels of Mcl-1 or PP5 or decreased levels of Huwe1 or CAS, regardless of p53 status (mutant or wild-type).

In one aspect, methods of treating a subject with a cancer having resistance to an inhibitor of tyrosine kinase activity by administering an inhibitor of tyrosine kinase activity and an inhibitor of E3 ubiquitin ligase MDM2 to the subject are provided.

In another aspect, methods of treating a subject with a cancer lacking wild-type p53 are provided. The methods include administering an MDM2 inhibitor in an effective amount to a subject with cancer lacking wild-type p53 to treat the cancer.

In yet another aspect, methods of treating a subject with a cancer having cells comprising increased levels of MDM2, Mcl-1 or PP5 or decreased levels of CAS or Huwe1 are provided. The methods include administering an MDM2 inhibitor in an effective amount to the subject to treat the cancer.

In a still further aspect, methods of screening for MDM2 inhibitors are provided. The methods include contacting cells with increased levels of Mcl-1 or PP5 or decreased levels of CAS or Huwe1 as compared to a control cell with an agent and determining the level of at least one of Mcl-1, PP5, CAS or Huwe1 in the cancer cell after contact with the agent. Agents capable of decreasing the level of Mcl-1 or PP5 or increasing the level of CAS or Huwe1 in the cells after contact with the agent as compared to the level in a control untreated cell are candidate inhibitors of MDM2 and may be effective cancer therapeutics.

In yet another aspect, methods of developing a treatment plan for an individual with cancer are provided. The methods include obtaining a sample comprising cancer cells from a subject and assaying the cells to determine the level of at least one of p53, MDM2, Mcl-1, PP5, CAS or Huwe1 in the cancer cells as compared to the level in control cells. A MDM2 inhibitor is administered to the subject if the cancer cells lack wild-type p53, have increased levels of MDM2, Mcl-1 or PP5 or have decreased levels of CAS or Huwe1 as compared to control cells.

BRIEF DESCRIPTION OF THE DRAWINGS

FIG. 3 is a set of photographs showing that Mcl-1 is stabilized in lapatinib-resistant cells.

FIG. 7 is a set of photographs and graphs showing PP5 stability and post-cytochrome c protection in lapatinib-resistant cells. FIG. 7B is a set of graphs showing Caspase 3 activity in the indicated cell lysates over time. Caspase-3 activity was assayed by measuring cleavage of DEVD-pNA following incubation of the cell lysates with 1 mM dATP and various concentrations of cytochrome c.

FIG. 9 is an autoradiograph (top) for ubiquitinylated PP5 or a photograph of an immunoblot (bottom) for Huwe1 showing biochemical purification of the PP5-targeted E3 ligase. Cell-free lysates (S100) prepared from SKBR3 cells were fractionated over a Q-sepharose column. Flow-through (FTQ) as well as bound proteins eluting at 100, 250, 500, 750, and 1000 mM NaCl (Q10, Q25, Q50, Q75, and Q100, respectively) were collected and dialyzed overnight. Ubiquitylation of PP5 was reconstituted in vitro by incubating $^{35}$S-methionine labeled PP5 (3 μl) with each Q-sepharose fraction (25 μl) supplemented with 1.5 ng/μl E1, 10 ng/μl UbcH7, 2.5 μg/μl ubiquitin (Ub), and an ATP-regenerating system in reaction buffer (50 mM Tris, pH7.6, 5 mM MgCl$_2$, 5 mMATP, 10 mM creatine phosphate, 3.5 U/ml creatine kinase; total reaction volume 40 μl). The reactions were incubated for 2 hours at 37° C. prior to analysis.

FIG. 10 is a set of photographs showing that Huwe1 is a PP5 ubiquitin ligase. FIG. 10A is an immunoblot for HA or PP5 after immunoprecipitation with HA. BT474 cells were transfected with empty vector or HA-tagged Huwe1 encoding residues 2473-4374 or the full-length protein and harvested after 24 hours. FIG. 10B is an immunoblot for Huwe1, PP5, Mcl1 and actin. BT474 cells were transfected with GFP- or Huwe1-specific siRNA (100 nM) and harvested after 72 hours. FIG. 10C is an immunoblot for PP5, Mcl-1, and Actin. BT474 cells were transfected with increasing amounts of wild type Huwe1 or its catalytically inactive mutant (Huwe1(C/S)) and the cells were harvested after 48 hours. FIG. 10D is an immunoblot for PP5 Ubiquitylation of PP5 was reconstituted in vitro by incubating recombinant PP5 protein with E1, UbcH7 (E2), ubiquitin (Ub), and recombinant Huwe1 protein (wild type (wt) or Huwe1(C/S)) in reaction buffer at 37° C. for 3 hours. FIG. 10E is a set of immunoblots for PP5 and Huwe1 after immunoprecipitation with FLAG antibodies. BT474 or rBT474 cells were transfected with FLAG-PP5 and the cells were treated with 1 µM lapatinib in the presence of z-VAD for 24 hours. Cells were harvested after treatment with 10 µM MG132 for 8 hours (*IgG heavy chain). FIG. 7F is an immunoblot for Apaf-1 and caspase-9. Cell lysates prepared from BT474 or rBT474 cells were incubated with or without 1 mM dATP and 10 ng/µl cytochrome c. After incubation (30 min), lysates were subjected to gel filtration (Superdex 200 column). Shown by asterisks is that a portion of Apaf-1 in the lapatinib-treated resistant cell lysate formed higher-order oligomers in response to cytochrome c.

FIG. 11 is a set of photographs of immunoblots showing CAS degradation in lapatinib-resistant cells.

FIG. 13 is a set of immunoblots showing MDM2-mediated ubiquitylation and degradation of Huwe1 in lapatinib-resistant cells.

FIG. 14 shows that MDM2 inhibition can reverse lapatinib resistance.

DETAILED DESCRIPTION

Figure 1:
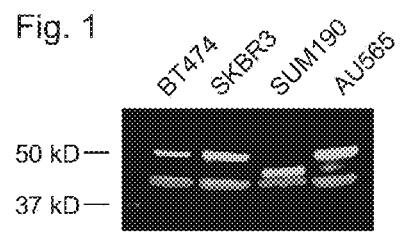
FIG. 1 is a photograph of a Western blot showing the level of p53 (top band) and actin (bottom band) expression in the cell lines used in the study. Three of the four cell lines have wild-type p53.
Figure 2A:
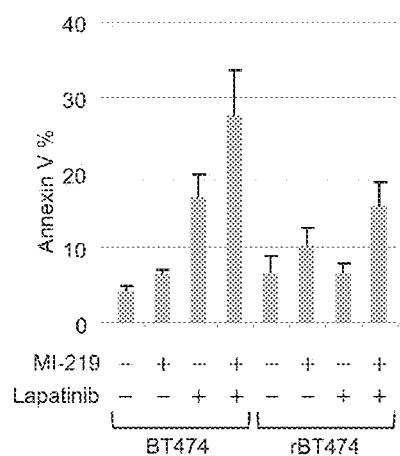
FIG. 2 is a set of graphs showing the percentage of cells undergoing apoptotic cell death for each of the four cell lines and their matched resistant cell line in the presence or absence of lapatinib and/or an MDM2 inhibitor, MI-219, as measured by FACS analysis for Annexin V. Results are expressed as mean +/− SEM of Annexin V positive cells. Graph A shows the results for BT474 and rBT474. Graph B shows the results for SKBR3 and rSKBR3. Graph C shows the results for AU565 and rAU565. Graph D shows the results for SUM190 and rSUM 190.
Figure 2C:
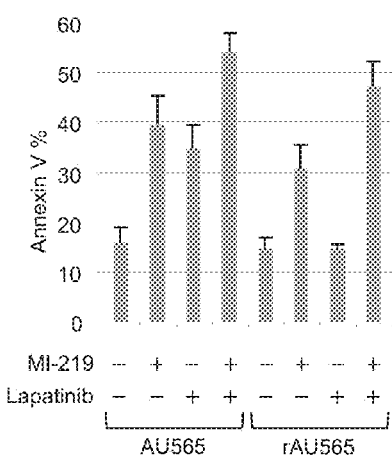
Figure 2B:
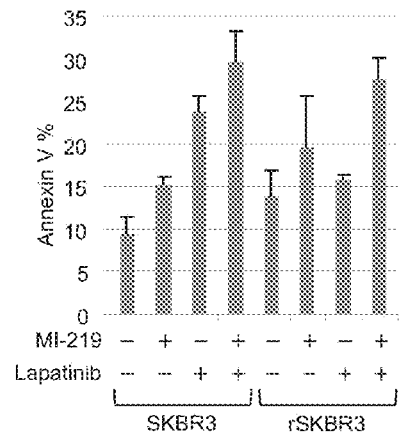
Figure 2D:
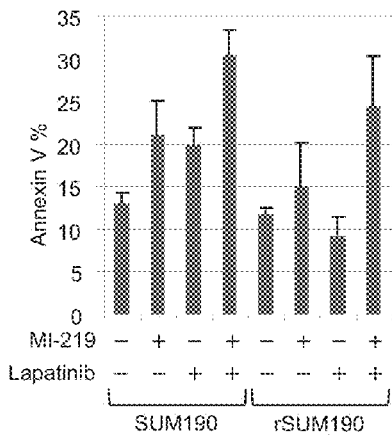

Methods of identifying or screening for MDM2 inhibitors and methods of treating subjects with cancer using MDM2 inhibitors, alone or in combination with other chemotherapeutics, are provided herein. MDM2 inhibitors are known and were developed for use in cancer patients with wild-type p53. See e.g., U.S. Pat. Nos. 7,834,016 and 7,759,383 and U.S. Patent Publication Nos. US2010/0216770; US2011/ 0130418, US2010/0168163 and US2010/0240637, each of which is incorporated herein by reference in its entirety. As demonstrated in the Examples, a new and unexpected mechanism of action for MDM2 inhibitors is disclosed herein and establishes the usefulness of MDM2 inhibitors to treat distinct cancers, i.e. those lacking wild-type p53 or comprising a p53 mutation, and to be used in distinct combinations with other chemotherapeutic agents than previously contemplated.

The Examples reveal an unexpected signaling network in which the MDM2 ubiquitin ligase could trans-ubiquitylate another E3 ligase, Huwe1, to control its substrates, Mcl-1 and protein phosphatase 5 (PP5), an indirect apoptosome regulator. As shown in the Examples, Huwe1 transmits a signal from MDM2 to control apoptotic events both upstream and downstream of mitochondria. Furthermore, MDM2 could ubiquitylate CAS, the requisite ATP exchange factor for Apaf-1. These MDM2-dependent pathways were subverted in lapatinib-resistant cells, and inhibition of MDM2 could rectify all apoptotic defects, overcoming drug resistance, regardless of cellular p53 status. Resistance to tyrosine kinase inhibitors, like lapatinib, often develops during treatment of cancer and although we have currently only demonstrated that this pathway is responsible for lapatinib resistance, it is likely a general resistance pathway and experiments are ongoing to demonstrate as much. As demonstrated below, treatment of a subject (a mouse) with cancer or a cancer cell with both lapatinib and an MDM2 inhibitor blocked the development of resistance and resulted in tumor regression or cancer cell death in either lapatinib resistant or sensitive cancer cells.

Therefore provided herein are methods of treating subjects with cancer. The cancer is generally a cancer with a mutation in a tyrosine kinase, overexpression of a tyrosine kinase or uncontrolled activity of a tyrosine kinase by autocrine paracrine stimulation such that the tyrosine kinase is more active than that of a control non-cancerous cell derived from the same or similar tissue as the cancer. The cancer may be a breast, lung, colon, gastric cancer or a glioma or leukemia. Suitably, the cancer does not have a wild-type p53. Suitably the cancer has wild-type p53. The subjects include mammals, including domesticated animals, mice, rats and humans.

Treating cancer includes, but is not limited to, reducing the number of cancer cells or the size of a tumor in the subject, reducing progression of a cancer to a more aggressive form, reducing proliferation of cancer cells or reducing the speed of tumor growth, killing of cancer cells, inducing apoptosis of cancer cells, reducing metastasis of cancer cells or reducing the likelihood of recurrence of a cancer in a subject. Treating a subject as used herein refers to any type of treatment that imparts a benefit to a subject afflicted with a disease or at risk of developing the disease, including improvement in the condition of the subject (e.g., in one or more symptoms), delay in the progression of the disease, delay the onset of symptoms or slowing the progression of symptoms, etc.

In one embodiment, the cancer is a cancer overexpressing a tyrosine kinase or with a mutation in a tyrosine kinase, such as HER2 or EGFR, and the cancer is resistant or likely to develop resistance to at least one inhibitor of tyrosine kinase activity. Resistance to an inhibitor of tyrosine kinase activity includes cancers and cells comprising a mutation in the targeted tyrosine kinase or a related gene such that the cells are able to survive and or continue to grow in the presence of an inhibitor of the tyrosine kinase and also includes cancers or cells that are at risk of developing resistance to the inhibitors. The subject may be treated by administering the inhibitor of tyrosine kinase activity and administering an inhibitor of E3 ubiquitin ligase, MDM2 (also called HDM2 in humans) to the subject.

Cancers overexpressing or having mutations in tyrosine kinases are well known in the art. The cancers often have an overactive tyrosine kinase. For example, tyrosine kinases whose over-activity is associated with cancer include, but are not limited to EGFR, IGFR, PDGFR, FGFR, SRC, mTOR, ABL, FAK, and Janus kinase. Suitably, the tyrosine kinase is a member of the HER or EGFR class of tyrosine kinases which includes EGFR, HER2, HER3 and HER4. Suitably, the kinase is HER2 or EGFR. The cancer may also be resistant to treatment with an antibody specific for the tyrosine kinase. For example, a HER2+ cancer may be resistant to treatment with trastuzumab.

The inhibitor of tyrosine kinase activity may be any inhibitor that targets the activity of the tyrosine kinase. The inhibitors include small molecule tyrosine kinase inhibitors, antibodies, antibody-drug conjugates, antisense oligonucleotides, aptamers, peptides and peptide mimetics. Tyrosine kinase inhibitors include flavoperidol, imatinib mesylate, erlotinib, gefitinib, dasatinib, lapatinib, lapatinib ditosylate, sorafenib, sunitinib, sunitinib maleate, temsirolimus. Suitably the inhibitor is an inhibitor of ATP binding to the tyrosine kinase. Suitably, the inhibitor of tyrosine kinase activity is lapatinib. Suitably, the inhibitor is an inhibitor of HER2 such as trastuzumab. Other anti-cancer agents may also be used in combination with MDM2 inhibitors.

The cells of the cancer being treated using the methods described herein may have increased MDM2, Mcl-1 or PP5 or decreased Huwe1 or CAS as compared to control cells. The cells may only have this differential expression after contact with a tyrosine kinase inhibitor. The control cells may be cancer cells that are not resistant to treatment with an inhibitor of tyrosine kinase activity, such as lapatinib, or non-cancerous cells of the same cell type as the cancer cells, i.e. derived from the same tissue. The cancer cells may only demonstrate the increased Mcl-1 or PP5 or decreased Huwe1 or CAS when in the presence of the inhibitor of tyrosine kinase activity. The transcription levels of Mcl-1 or PP5 or Huwe1 or CAS may be unchanged and the difference in levels of these markers in the cancer cell is due to increased stability of the proteins or decreased degradation of the proteins.

The levels of these proteins in cancer cells may be measured via methods available to those of skill in the art. For example, the level of MDM2, Mcl-1, PP5, CAS or Huwe1 in the cells may be determined by methods including but not limited to Western blot, FACs analysis, immunoprecipitation, radiolabeling, fluorescence labeling or other antibody based-detection assay. The level of these markers being determined is the protein level, not the level of transcription. The stability of these proteins may also be determined rather than the level at any point in time. Stability of the proteins may be assessed using methods available to those skilled in the art, such as pulse-chase experiments followed by one of the above methods to separate the proteins from the cell.

The MDM2 inhibitors include any inhibitors capable of blocking the interaction of MDM2 with a target molecule such as p53, Huwe1 and CAS, capable of inhibiting the ubiquitin ligase activity of MDM2, an inhibitor of MDM2 transcription or translation or a molecule capable of decreasing the half-life of MDM2 in the cell. The MDM2 inhibitors may be small molecule pharmaceuticals, RNA-based molecules such as an shRNA or siRNA, an aptamer or antibody or any other class of inhibitory molecule. Several MDM2 inhibitors have been previously described as noted above.

Two small molecule inhibitors used in the Examples are nutlin-3a and MI-219, a spiro-oxindole. A siRNA and an shRNA that target MDM2 were also found to be effective inhibitors in the Examples.

Methods of treating a subject with a cancer overexpressing or having a mutation in a tyrosine kinase, such as HER2, by administering an inhibitor of tyrosine kinase activity and administering an inhibitor of MDM2 to the subject are provided. The inhibitor of tyrosine kinase activity and the inhibitor of MDM2 may be administered in any order, at the same time or as part of a unitary composition. The two inhibitors may be administered such that one inhibitor is administered before the other with a difference in administration time of 1 hour, 2 hours, 4 hours, 8 hours, 12 hours, 16 hours, 20 hours, 1 day, 2 days, 4 days, 7 days, 2 weeks, 4 weeks or more.

In another embodiment, methods of treating a subject with a cancer in which at least some of the cells of the cancer lack wild-type p53 or have a p53 mutation and optionally comprise a mutation in or overexpression of a tyrosine kinase are provided. In these methods, an MDM2 inhibitor is administered in an effective amount to treat a subject with a cancer lacking wild-type p53 or having a p53 mutation. In these methods, the p53 status of the cancer may be determined prior to treating the subject with the MDM2 inhibitor.

In another embodiment, methods of treating subjects with cancers in which at least some of the cancer cells have increased levels of Mcl-1 or PP5 or decreased levels of CAS or Huwe1 as compared to the levels of these markers in control cells. As noted above, control cells may be cancerous cells sensitive to tyrosine kinase inhibitors, such as lapatinib or non-cancerous cells. In these methods, an MDM2 inhibitor is administered to a subject in an amount effective to treat the cancer. In these methods, an inhibitor of tyrosine kinase activity may also be administered to the subject to treat the cancer. As noted above, the two inhibitors may be provided separately, at the same time or even within the same composition. The protein expression levels of at least one of MDM2, Mcl-1, PP5, Huwe1 or CAS may be determined prior to initiating treatment. Those of skill in the art will appreciate that several methods exist to assess the level of each of these proteins within the cell, some of which are discussed above.

An effective amount or a therapeutically effective amount as used herein means the amount of a compound that, when administered to a subject for treating a state, disorder or condition is sufficient to effect a treatment (as defined above). The therapeutically effective amount will vary depending on the compound, formulation or composition, the disease and its severity and the age, weight, physical condition and responsiveness of the subject to be treated.

Compositions comprising the inhibitors described herein may be administered by any means known to those skilled in the art, including, but not limited to, oral, topical, intranasal, intraperitoneal, parenteral, intravenous, intraarterial, intramuscular, sublingual, or subcutaneous. Thus the compositions may be formulated as an ingestable, injectable, topical or suppository formulation. The compositions may also be delivered with in a liposomal or time-release vehicle. Administration of the compositions to a subject in accordance with the invention appears to exhibit beneficial effects in a dose-dependent manner. Thus, within broad limits, administration of larger quantities of the compositions is expected to achieve increased beneficial biological effects than administration of a smaller amount. Moreover, efficacy is also contemplated at dosages below the level at which severe toxicity is seen.

It will be appreciated that the specific dosage administered in any given case will be adjusted in accordance with the compositions being administered, the disease to be treated or inhibited, the condition of the subject, and other relevant medical factors that may modify the activity of the compositions or the response of the subject, as is well known by those skilled in the art. For example, the specific dose for a particular subject depends on age, body weight, general state of health, diet, the timing and mode of administration, the rate of excretion, medicaments used in combination and the severity of the particular disorder to which the therapy is applied. Dosages for a given patient can be determined using conventional considerations, e.g., by customary comparison of the differential activities of the compositions such as by means of an appropriate conventional pharmacological or prophylactic protocol.

The maximal dosage for a subject is the highest dosage that does not cause undesirable or intolerable side effects. The number of variables in regard to an individual treatment regimen is large, and a considerable range of doses is expected. The route of administration will also impact the dosage requirements. It is anticipated that dosages of the composition will reduce growth of the cancer by at least 10%, 20%, 30%, 40%, 50%, 60%, 70%, 80%, 90% or 100% compared to a cancer left untreated. It is specifically contemplated that pharmaceutical preparations and compositions may palliate or alleviate symptoms of the disease without providing a cure, or, in some embodiments, may be used to cure the disease or disorder.

Suitable effective dosage amounts for administering the compositions may be determined by those of skill in the art, but typically range from about 1 microgram to about 10,000 micrograms per kilogram of body weight weekly, although they are typically about 1,000 micrograms or less per kilogram of body weight weekly. In some embodiments, the effective dosage amount ranges from about 10 to about 10,000 micrograms per kilogram of body weight weekly. In another embodiment, the effective dosage amount ranges from about 50 to about 5,000 micrograms per kilogram of body weight weekly. In another embodiment, the effective dosage amount ranges from about 75 to about 1,000 micrograms per kilogram of body weight weekly. The effective dosage amounts described herein refer to total amounts administered, that is, if more than one composition is administered, the effective dosage amounts correspond to the total amount administered. The compositions can be administered as a single dose or as divided doses. For example, the composition may be administered two or more times separated by 4 hours, 6 hours, 8 hours, 12 hours, a day, two days, three days, four days, one week, two weeks, or by three or more weeks.

Methods of screening for MDM2 inhibitors capable of being used as cancer therapeutic agents are also provided herein. The methods include contacting a cancer cell with an agent and determining the protein expression level of at least one of MDM2, Mcl-1, PP5, CAS or Huwe1 in the contacted cancer cell. The cancer cells have higher than normal levels of MDM2, Mcl-1 or PP5 or lower than normal levels of CAS or Huwe1 as compared to control cells, in particular after the cells are contacted with an inhibitor of tyrosine kinase activity, such as lapatinib.

Notably, the cancer cells may overexpress or comprise a mutation in a tyrosine kinase such as HER2 or EGFR and may be resistant to lapatinib or other tyrosine kinase inhibitors. An agent capable of decreasing the levels of MDM2, Mcl-1 or PP5 or of increasing the level of Huwe1 or CAS in the cells after contact with the agent as compared to the level in a control cell is a candidate MDM2 inhibitor. Control cells may be cancer cells that are not resistant to the tyrosine kinase inhibitor or non-cancerous cells. Untreated cells are cancer cells prior to treatment with the agent. In the methods of screening, the cells may be contacted with lapatinib prior to or at the same time as the cells are contacted with the agent.

Cells may be contacted with the agent directly or indirectly in vivo, in vitro, or ex vivo. Contacting encompasses administration to a cell, tissue, mammal, patient, or human. Further, contacting a cell includes adding an agent to a cell culture. Other suitable methods may include introducing or administering an agent to a cell, tissue, mammal, or patient using appropriate procedures and routes of administration as defined above.

The level of MDM2, Mcl-1, PP5, CAS or Huwe1 in the cells may be determined by any method known to those of skill in the art, including but not limited to Western blot, FACs analysis, immunoprecipitation, radiolabeling, fluorescence labeling. The level of these markers being determined is the protein level, not the level of transcription. The stability of these proteins may also be determined rather than the level at any point in time.

Methods of developing treatment plans for individuals with cancer are also provided. The treatment plans are meant to avoid allowing the cancer to become resistant to tyrosine kinase inhibitors and/or to allow treatment of a cancer that is resistant to treatment with a tyrosine kinase inhibitor. The methods include obtaining a sample comprising cancer cells from a subject and assaying the cells to determine the level of at least one of MDM2, Mcl-1, PP5, CAS or Huwe1 in the cancer cells as compared to the level in control cells. Suitably the control cells are non-cancerous cells from a similar or from the same tissue or cell-type. If the cancer cells have increased levels of MDM2, Mcl-1 or PP5 or has decreased levels of CAS or Huwe1 as compared to the control cells, then the treatment plan for the subject includes administration of a MDM2 inhibitor to the subject. In one embodiment, the level of more than one of MDM2, Mcl-1, PP5, CAS and Huwe1 are assayed. In another embodiment, the level of all of MDM2, Mcl-1, PP5, CAS and Huwe1 are assayed. The treatment plan may also include administering a tyrosine kinase inhibitor to the subject.

The following examples are meant only to be illustrative and are not meant as limitations on the scope of the invention or of the appended claims. All references cited herein are hereby incorporated by reference in their entireties.

EXAMPLES

Mcl-1 Stabilization in Lapatinib-Resistant Breast Cancer Cells

Figure 3A:
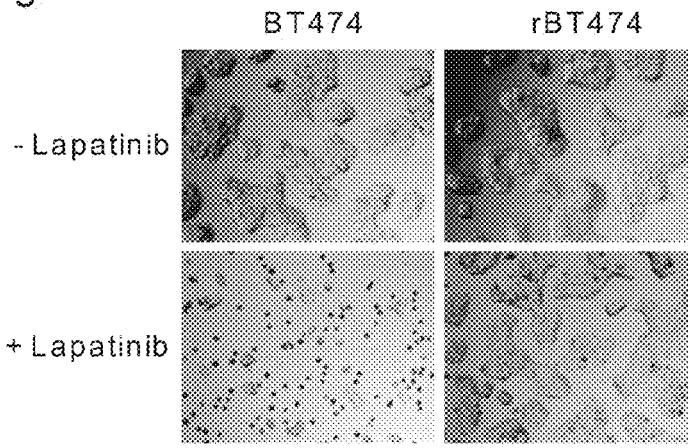
FIG. 3A is a photomicrograph of lapatinib-sensitive and resistant BT474 cells (BT474 and rBT474, respectively) treated with 1 μM lapatinib for 48 hours.
Figure 3B:
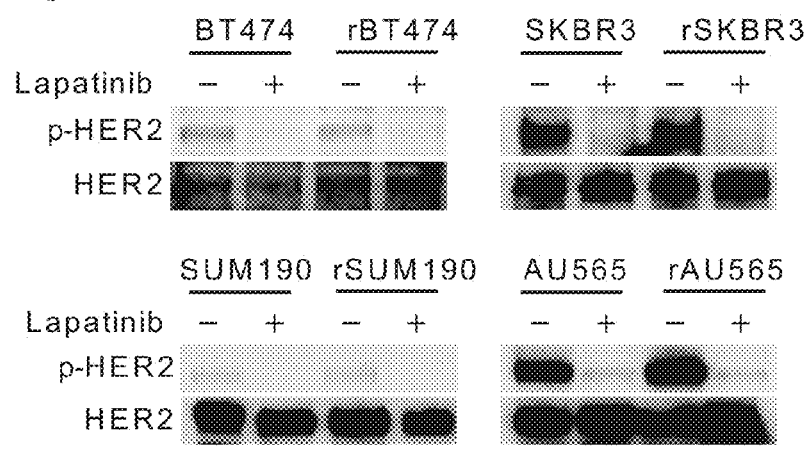
FIG. 3B is a set of immunoblots showing the levels of HER2 and phospho-HER2 in untreated cells and cells treated with lapatinib. Cells were treated with or without lapatinib (1 μM) for 24 hours in the presence of the caspase inhibitor z-VAD (50 μM). The cells were harvested and cell lysates were immunoblotted using antibodies against phospho-HER2 (Y877) and total HER2.
Figure 3C:
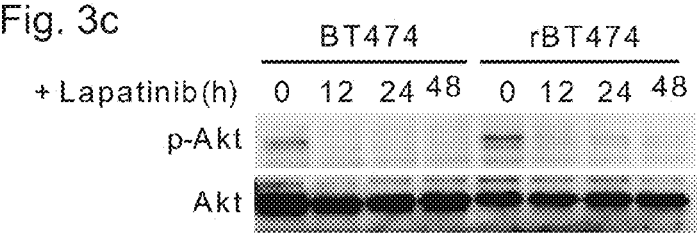
FIG. 3C is an immunoblot for phospho-AKT (T308) and total AKT. BT474 and rBT474 cells were treated with 1 μM lapatinib in the presence of 50 μM z-VAD. At the indicated time points, the cells were harvested and immunoblotted.
Figure 3D:
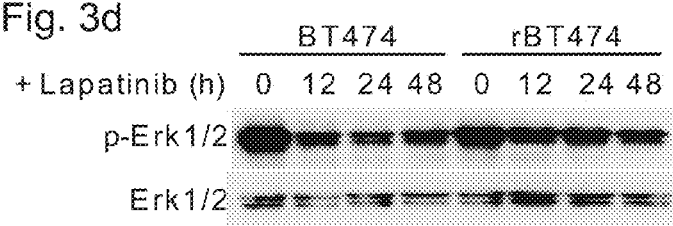
FIG. 3D is an immunoblot for phospho-Erl1/2(T202/Y204) and total Erk1/2. BT474 and rBT474 cells were treated with 1 μM lapatinib in the presence of 50 μM z-VAD. At the indicated time points, the cells were harvested and immunoblotted.

To analyze molecular mechanisms underlying lapatinib-resistance, four independent lapatinib-resistant HER2-positive breast cancer cell lines were derived by continuous culture of BT474, SKBR2, SUM 190 and AU565 cells in the presence of lapatinib. Xia, W. et al. *Proc. Natl. Acad. Sci. USA* 103, 7795-7800 (2006). Regardless of estrogen receptor (ER), progesterone receptor (PR), or p53 status, all four parental sensitive cell lines died from apoptosis in response to lapatinib. See FIG. 1 and Table 1. All four resistant lines (hereafter referred to as rBT474, rSKBR2, rSUM190, and rAU565) did not die in response to lapatinib treatment (FIG. 2 and FIG. 3A). Lapatinib inhibited HER2 tyrosine autophosphorylation even in resistant cells (FIG. 3B). Furthermore, phosphorylation of both Akt and Erk1/2, two primary downstream effectors in HER2-overexpressing breast cancer, were also attenuated in sensitive and resistant cells treated with lapatinib (FIGS. 3C and 3D). Akt inhibition was unable to reverse lapatinib resistance.

TABLE 1

Pathological features of breast cancer cell lines used in this study

| Cell Line | HER2* | ER* | PR* | P53# | Tumor Type* |
|---|---|---|---|---|---|
| AU 565$^a$ | + | − | − | WT | AC |
| BT474 | + | + | + | M AA285: Glu→Lys | IDC |
| SKBR3$^a$ | + | − | − | M AA175: Arg→His | AC |
| SUM190PT | + | − | − | M AA317: Gln→STOP | Inf |

Abbreviations:
AC = adenocarcinoma;
ER = estrogen receptor;
IDC = invasive ductal carcinoma;
Inf = inflammatory carcinoma;
PR = progesterone receptor
*from the ATCC (http://www.atcc.org).
from the IARC TP53 database (http://www-p53.iarc.fr/). WT = wild type, M = mutant.
$^a$AU565 and SKBR3 were isolated from the same patient.

Figure 3E:
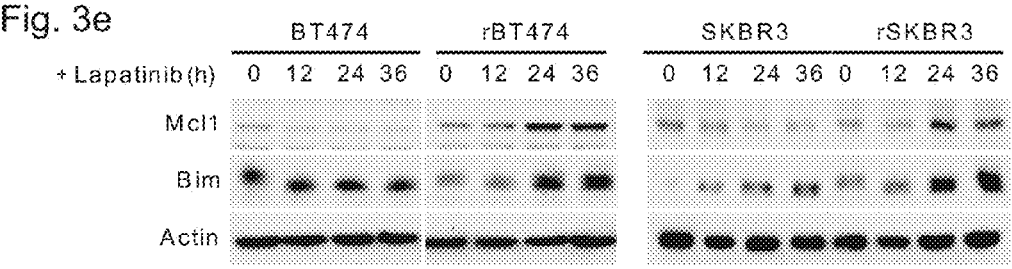
FIG. 3E is an immunoblot for Mcl-1, Bim, and Actin. BT474 and rBT474 cells (left) or SKBR3 and rSKBR3 cells (right) were treated with 1 μM lapatinib. The cells were harvested at the indicated time points and immunoblotted.
Figure 4:
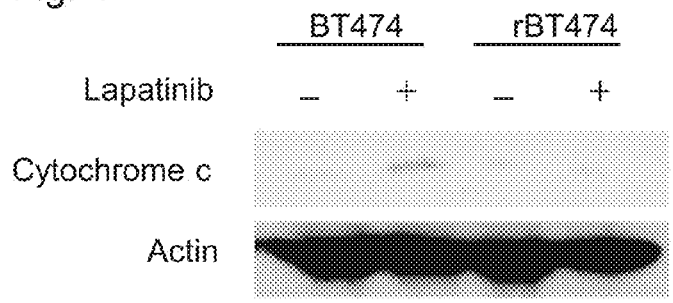
FIG. 4 is a photograph of a Western blot for cytochrome c and actin in cytosolic lysates lacking mitochondria. BT474 and rBT474 cells were treated with 1 μM lapatinib or without any drug for 24 hours. The rBT474 cells prevent mitochondrial cytochrome c release in response to treatment with lapatinib.

Since lapatinib promotes tumor regression at least in part by inducing apoptosis, we speculated that resistant cells might have altered apoptotic signaling. Indeed, lapatinib induced mitochondrial cytochrome c release in parental BT474 cells, but not rBT474 cells (FIG. 4), suggesting that pro- and anti-apoptotic Bcl-2 family proteins that govern the mitochondrial outer membrane permeability might be modulated in the lapatinib-treated resistant cells. While we observed no significant difference in expression of multiple Bcl-2 family members (e.g. Bim, FIG. 3E) between sensitive and resistant cells, the anti-apoptotic Bcl-2 member Mcl-1 was significantly upregulated in the resistant breast cancer cells treated with lapatinib (FIG. 3E). In the sensitive cells, Mcl-1 protein levels decreased upon treatment with lapatinib, whereas Mcl-1 protein levels increased in the resistant cells in the presence of lapatinib (FIG. 3E).

Figure 3F:
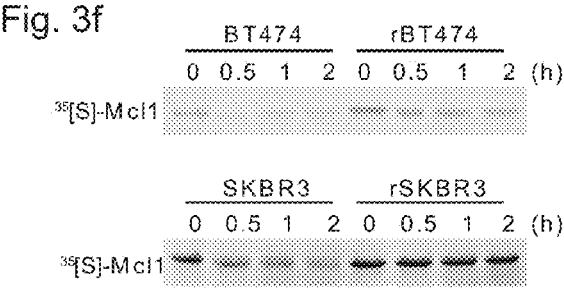
FIG. 3F is an autoradiograph showing the $^{35}$[S] radioactivity in lysates containing $^{35}$[S]-Mcl-1 at the indicated time points. $^{35}$[S]-labeled Mcl-1 protein was incubated in cell-free lysates prepared from BT474 and rBT474 cells (top) or SKBR3 and rSKBR3 cells (bottom).
Figure 3G:
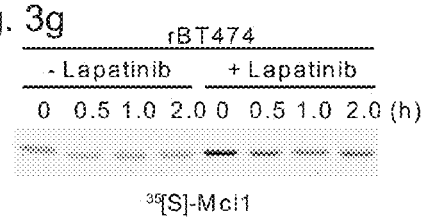
FIG. 3G is an autograph showing the $^{35}$[S]-labeled Mcl-1 to monitor Mcl-1 stability over time. The $^{35}$[S]-labeled Mcl-1 was incubated in lysates prepared from rBT474 cells treated with or without 1 μM lapatinib.
Figure 3H:
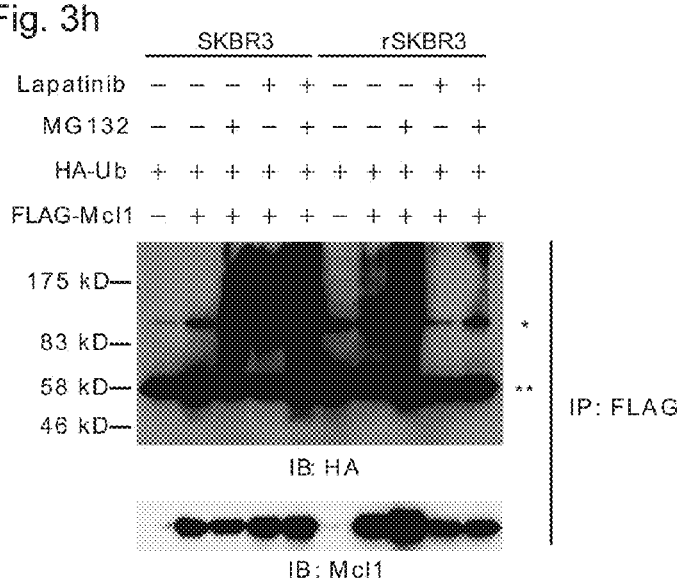
FIG. 3H is an immunoblot for HA. SKBR3 or rSKBR3 cells were co-transfected with FLAG-Mcl-1 and HA-Ubiquitin (Ub). Cells were treated with 1 μM lapatinib for 24 hours in the presence of z-VAD. Cells were harvested after treatment with 10 μM MG 132 for 4 hours. FLAG-Mcl-1 was retrieved by immunoprecipitation using anti-flag agarose, and Mcl-1 ubiquitylation was analyzed by immunoblotting for HA (*non-specific band, **IgG heavy chain).
Figure 5:
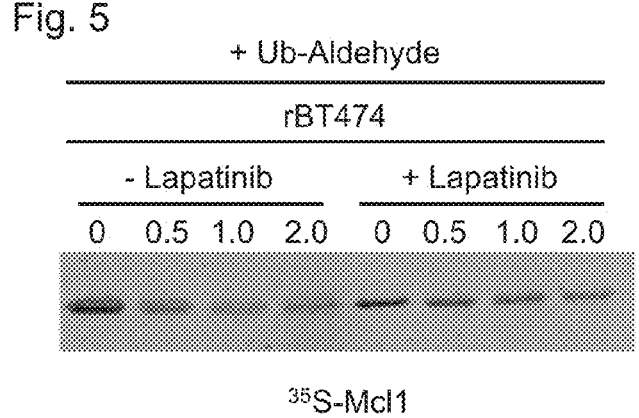
FIG. 5 is an autoradiograph showing the stability of $^{35}$[S]-labeled Mcl-1 in rBT474 cell lysates after the cells were treated with or without 1 μM lapatinib and 5 μM ubiquitin aldehyde (UB-Aldehyde) and incubated for 30 minutes.

Rapid degradation of $^{35}$[S]-Mcl-1 was observed in cell-free lysates prepared from sensitive cells, while this degradation was blocked in resistant lysates (FIG. 3F). These results indicate that the observed differences in Mcl-1 abundance stemmed from differences in Mcl-1 stability. A similar stabilization was observed in the presence of the proteasome inhibitor, MG 132. Importantly, although the Mcl-1 protein half-life was prolonged in resistant cell lysates, this was only observed in lysates from cells treated with lapatinib (e.g., lapatinib-treated rBT474 cells, FIG. 3G). Addition of ubiquitin aldehyde, a deubiquitylase inhibitor, to the lysates did not prevent the failure to degrade $^{35}$[S]-Mcl-1 in resistant cells (FIG. 5), suggesting that Mcl-1 stabilization might be secondary to a defect in Mcl-1 ubiquitylation, rather than enhanced deubiquitylation. To examine Mcl-1 ubiquitylation directly, we co-transfected FLAG-tagged Mcl-1 together with HA-tagged ubiquitin, and examined Mcl-1 ubiquitylation by anti-HA antibody following immunoprecipitation of FLAG-Mcl-1. In the absence of lapatinib, Mcl-1 protein was equally ubiquitylated in SKBR3 and rSKBR3 cells (FIG. 3H). Lapatinib treatment enhanced Mcl-1 ubiquitylation in SKBR3 cells; but diminished Mcl-1 ubiquitylation in rSKBR3 cells (FIG. 3H). These data suggest that upregulation of Mcl-1 protein in the lapatinib-resistant cells might result from a lapatinib-dependent defect in the Mcl-1 ubiquitylation machinery.

Incorrect Apoptosome Assembly in Lapatinib-Resistant Cells

Figure 6:
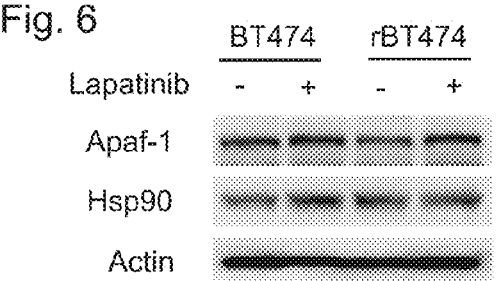
FIG. 6 is a photograph of an immunoblot for Apaf-1, Hsp90β or actin in cell lysates of BT474 and rBT474 cells after treatment with no drug or 1 μM lapatinib for 24 hours in the presence of the caspase inhibitor z-VAD (50 μM) showing expression was not altered.
Figure 7A:
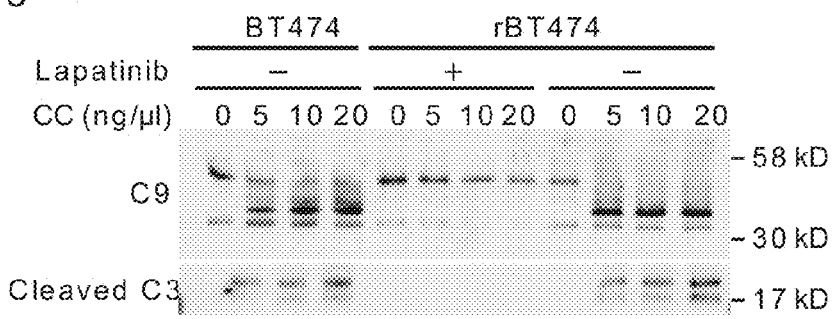
FIG. 7A is an immunoblot for caspase-9 (cleaved and non-cleaved) and cleaved caspase-3 (C9 and C3, respectively) showing rBT474 cells cultured in the absence or presence of 1 μM lapatinib for one week, as compared to BT474 cells which were maintained without lapatinib. Cytosolic lysates prepared from BT474 or rBT474 were incubated with 1 mM dATP and various amounts of cytochrome c (CC).
Figure 7C:
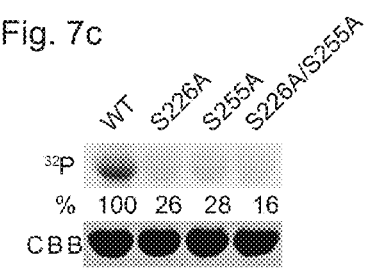
FIG. 7C is an autoradiograph of $^{32}$P and an immunoblot showing the percentage of the protein phosphorylated. In the presence of [γ-$^{32}$P]ATP, recombinant His-tagged HSP90β proteins (wild type and the indicated mutants) on nickel beads were incubated with the HSP90β-targeted kinase casein kinase 2.
Figure 7D:
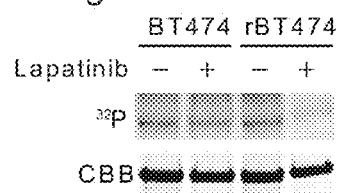
FIG. 7D is an autoradiograph and corresponding immunoblot showing BT474 or rBT474 cells after being cultured in the absence or presence of 1 μM lapatinib for 24 hours in the presence of z-VAD. Recombinant His-tagged HSP90β protein on nickel beads was incubated with the cell lysates in the presence of [γ-$^{32}$P]ATP.
Figure 7E:
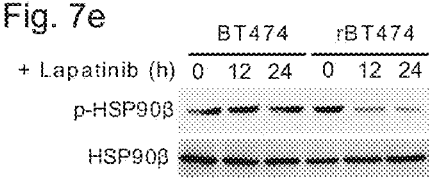
FIG. 7E is an immunoblot for phospho-Hsp90β (Ser226) and total HSP90β at various time points. BT474 or rBT474 cells were treated with 1 μM lapatinib for the indicated amount of time.
Figure 7F:
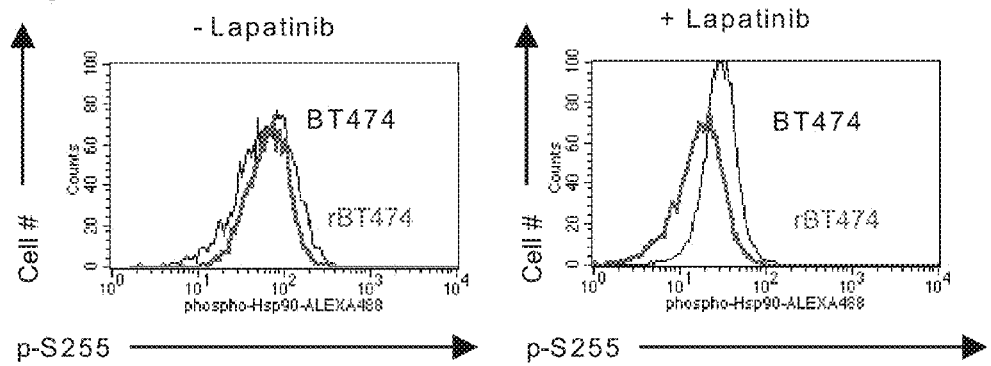
FIG. 7F is a set of graphs showing FACS analysis for the phosphorylation status of Hsp90β (Ser255). BT474 or rBT474 cells cultured in the presence of 1 μM lapatinib for 24 hours were fixed with formaldehyde and incubated with phospho-Hsp90β (Ser255) antibody followed by an Alexa488-conjugated secondary antibody.

In analyzing the mechanism of lapatinib resistance, we noted that the resistant cells failed to activate caspases when purified cytochrome c was added directly to lysates. Cytochrome c induced robust caspase activation in parental cells, though Apaf-1, caspase-9 and caspase-3 levels were similar in resistant and sensitive cells (FIG. 6 and FIG. 7A). As we observed for Mcl-1 protein stability, the failure of cytochrome c to induce caspase activation in lapatinib-resistant cells was "lapatinib-dependent." When resistant cells were cultured in the presence of lapatinib, the lysates exhibited strong defects in caspase activation. When lapatinib was removed from the culture medium, lysates could respond to cytochrome c (FIGS. 7A and 7B).

PP5 Stabilization in Lapatinib-Resistant Breast Cancer Cells

HSP90β binds directly to the Apaf-1 CARD domain to block caspase-9 recruitment. We found that this inhibition was significantly increased in leukemic cells where HSP90β hypophosphorylation at residues Ser226 and Ser255 led to tighter interaction between Apaf-1 and HSP90β. Kurokawa, M., Zhao, C., Reya, T. & Kornbluth, S. *Mol. Cell. Biol.* 28, 5494-5506 (2008). Interestingly, HSP90β phosphorylation at both Ser226 and Ser255 was also markedly decreased in lapatinib-treated resistant cells compared to sensitive cells (FIGS. 7C-7F).

Figure 7G:
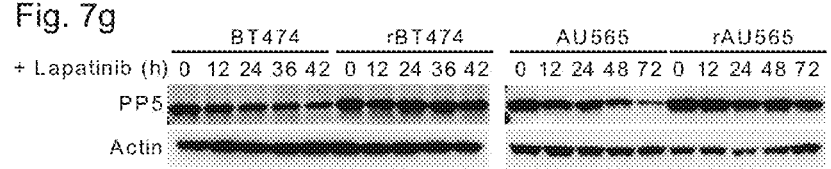
FIG. 7G is an immunoblot for PP5 and actin at the indicated time points. BT474 and rBT474 (left) or AU565 and rAU565 cells (right) were treated with 1 μM lapatinib.
Figure 7H:
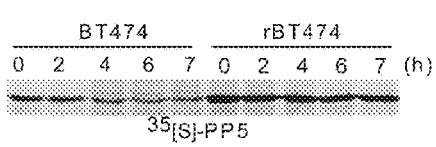
FIG. 7H is an autoradiograph of immunoprecipitated FLAG-PP5 using an anti-FLAG agarose. BT474 or rBT474 cells were transfected with FLAG-PP5 and subsequently labeled by the addition of $^{35}$[S]-Met. Cells were cultured in the presence of lapatinib and harvested at various time points after addition of lapatinib.
Figure 7I:
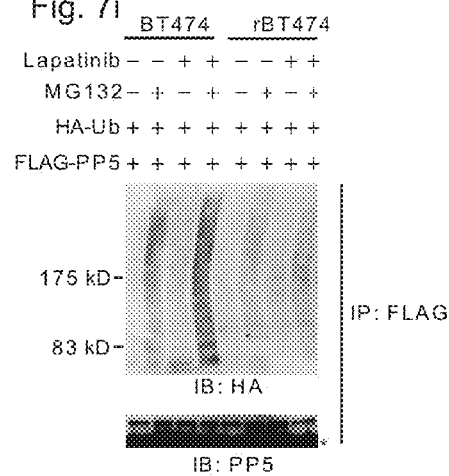
FIG. 7I is an immunoblot for HA or PP5 after immunoprecipitation using anti-FLAG agarose. BT474 or rBT474 cells were co-transfected with FLAG-PP5 and HA-Ub. Cells were cultured in the presence or absence of 1 μM lapatinib for 24 hours. Cells were harvested after treatment with 10 μM MG132 for 8 hours (*IgG heavy chain).
Figure 8:
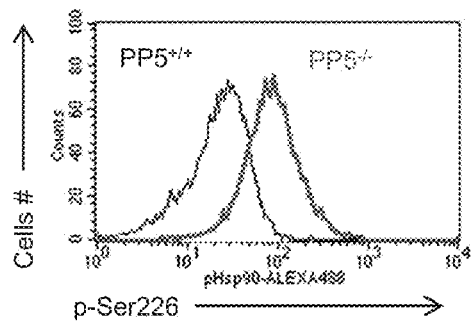
FIG. 8 is a set of graphs showing FACS analysis for phosphorylation of Hsp90β in MEFs derived from wild-type (PP5$^{+/+}$) or PP5 deficient (PP5$^{-/-}$) mice after incubation with either a phospho-S226 or a phospho-S255 Hsp90 antibody followed by an Alexa488 conjugated secondary antibody.
Figure 8:
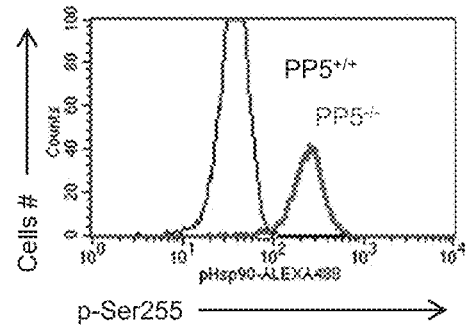

Since lapatinib did not prevent HSP90β phosphorylation in normal BT474 cells (FIG. 7D), lapatinib was unlikely to inhibit an HSP90β-directed kinase (e.g., casein kinase 2). These data suggest that an HSP90β-directed phosphatase might be modulated in response to lapatinib. PP5 regulates the phosphorylation of HSP90 in other settings. Wandinger, S. K., Suhre, M. H., Wegele, H. & Buchner, J. *EMBO J.* 25, 367-376 (2006). We confirmed that the phosphorylation of Ser226 and Ser255 was significantly increased in PP5$^{-/-}$ mouse embryonic fibroblasts (MEFs) when compared with phosphorylation at these sites in wild type MEFs (FIG. 8). Therefore, we hypothesized that hypophosphorylation of HSP90β in lapatinib-resistant cells might result from upregulation of HSP90β-directed PP5 activity. We found that lapatinib treatment triggered a gradual decrease in PP5 levels in sensitive cells, whereas levels were unaltered in resistant cells (FIG. 7G). Indeed, the protein half-life of PP5 was significantly longer in resistant cells than in the parental cells (FIG. 7H). Accordingly, PP5 was much more highly ubiquitylated in sensitive than resistant cells (FIG. 7I). Taken together, these results suggest that hypophosphorylation of HSP90β in resistant cells may be attributable to enhanced PP5 stability.

Huwe1 is an E3 Ligase Responsible for the Degradation of Both Mcl-1 and PP5

PP5 stabilization could result from a defect in an E3 ligase activity responsible for PP5 ubiquitylation in lapatinib-resistant cells. Hence, we sought to identify a PP5-directed E3 ligase through chromatographic purification. Cytosolic lysates prepared from SKBR3 cells were fractionated on a Q-sepharose column and ubquitylation of $^{35}$[S]-PP5 by each fraction (supplemented with E1, E2, ATP and ubiquitin) was analyzed by SDS-PAGE. Most of the PP5-ubiquitinating activity was eluted with 500 mM NaCl (FIG. 9). Given that we had already found changes in Mcl-1 stability in response to lapatinib, we speculated that a known Mcl-1-directed E3 ubiquitin ligase might also regulate PP5 stability. Indeed, immunoblotting of Q-sepharose fractions revealed that Huwe1 (also known as Mule, ARF-BP1, HectH9), an HECT-domain E3 ligase known to target Mcl-1 for degradation, was also eluted with 500 mM NaCl, corresponding to the fraction with the PP5-ubiquitylating activity (FIG. 9).

In agreement with these observations, we found that HA-Huwe1 co-immunoprecipitated with endogenous PP5 (FIG. 10A). Moreover, knockdown of Huwe1 using siRNA increased both PP5 and Mcl-1 levels in BT474 cells (FIG. 10B). Conversely, overexpression of HA-Huwe1, but not catalytically inactive HA-Huwe1(C/S), reduced PP5 and Mcl-1 protein levels (FIG. 10C). We obtained the same results in HeLa cells and the p53-null H1299 cells. As shown in FIG. 10D, in the presence of both E1 and E2, wild type recombinant Huwe1 protein, but not Huwe1(C/S), ubiquitylated recombinant PP5 in vitro (FIG. 10D). These results suggested that the enhanced protein stability of PP5 and Mcl-1 observed in the resistant cells was due to a defect in protein ubiquitylation mediated by Huwe1 (see further in FIG. 13, below).

Downregulation of CAS in Lapatinib-Resistant Cells

HSP90β hypophosphorylation downstream of PP5 stabilization might explain apoptosome inhibition in the lapatinib-treated resistant cells, but when we resolved cell lysates by gel filtration, we saw not only a failure to recruit caspase-9 to Apaf-1 (which could be explained if HSP90β blocked caspase 9 recruitment), but also a failure of the majority of Apaf-1 to oligomerize (FIG. 10F). Moreover, upon addition of cytochrome c to resistant cell lysates, we detected a small percentage of Apaf-1 and caspase-9 in very large (1,000-1400 kD) fractions, previously described as incorrectly assembled inactive complexes (FIG. 10F; shown by asterisks). Kim, Jiang, Du, & Wang, *Mol. Cell* 30, 239-247 (2008).

Figure 11A:
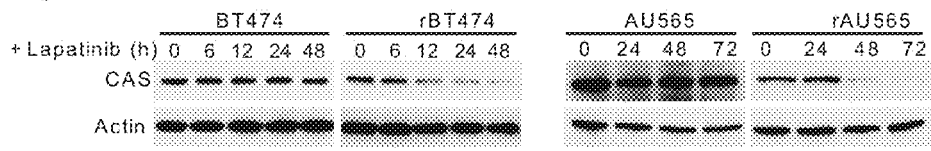
FIG. 11A is an immunoblot for CAS and Actin. BT474 and rBT474 (left) or AU565 and rAU565 cells (right) cultured in the absence of lapatinib for one week were treated with 1 µM lapatinib and the cells were harvested at various time points.
Figure 11B:
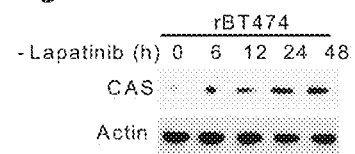
FIG. 11B is an immunoblot for CAS and Actin. rBT474 cells were maintained in the presence of 1 M lapatinib and the cells were harvested at various time points following removal of lapatinib.
Figure 11C:
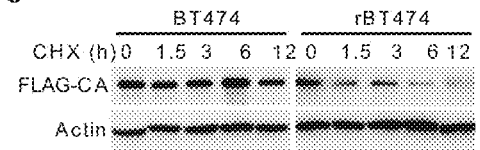
FIG. 11C is an immunoblot for FLAG and actin. BT474 and rBT474 cells were transiently transfected with FLAG-tagged CAS and subsequently treated with 50 µg/ml cycloheximide (CHX) and 1 µM lapatinib and the cells were harvested at various time points.
Figure 11D:
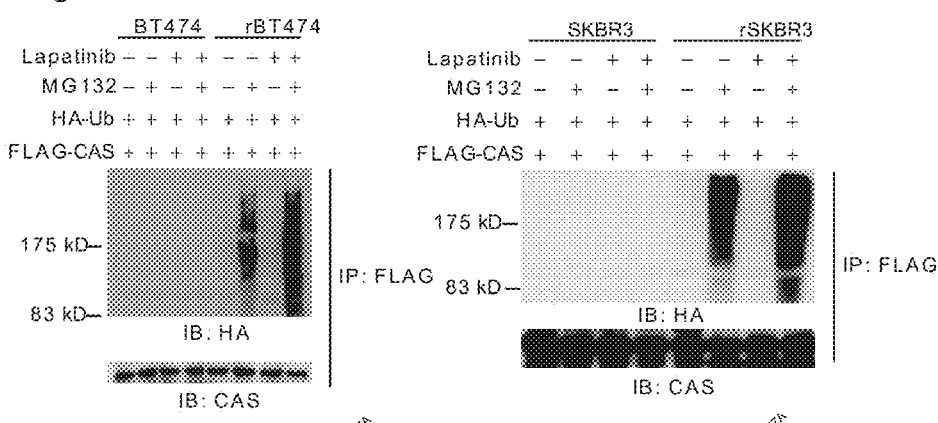
FIG. 11D is an immunoblot using HA to analyze ubiquitination of CAS. BT474 and rBT474 (left) or SKBR3 and rSKBR3 cells (right) were co-transfected with FLAG-CAS and HA-Ub. Cells were treated with 1 µM lapatinib for 24 hours in the presence of z-VAD. After treatment with 10 µM MG 132 for 8 hours, cells were harvested and FLAG-CAS was retrieved by immunoprecipitation.

Without nucleotide exchange, cytochrome c induces Apaf-1 to form non-functional aggregates. Accordingly, we examined protein levels of PHAP1, HSP70, and CAS (also known as CSE1L or Exportin-2), essential components of the nucleotide exchange factor required for loading Apaf-1 with dATP. Whereas PHAP1 and HSP70 levels did not differ between parental and resistant cells, CAS protein levels were markedly decreased in resistant cells compared with parental cells, most notably in the presence of lapatinib (see FIG. 11A). CAS protein levels declined over time following lapatinib addition to resistant cells, but lapatinib removal allowed return of CAS to levels comparable to the parental cells (FIGS. 11A and 11B). Treatment of parental cells with lapatinib did not affect CAS protein levels (FIG. 11A). In addition, in breast cancer cell lines that are non-responsive to lapatinib due to low expression of HER2 (e.g., T47D cells), lapatinib treatment did not alter CAS protein levels. Quantitative real-time PCR demonstrated that lapatinib did not cause a reduction in CAS mRNA levels in either sensitive or resistant cells. However, CAS protein was stabilized in sensitive cells, but destabilized in lapatinib-treated resistant cells (FIG. 11C). Accordingly, ubiquitylation of CAS was nearly undetectable in sensitive cells even in the presence of MG132, while CAS ubiquitylated species were readily detected in resistant cells and more prominent in the presence of lapatinib (FIG. 11D). These data suggest that CAS downregulation in lapatinib-resistant cells results from augmented CAS protein ubiquitylation.

Figure 11E:
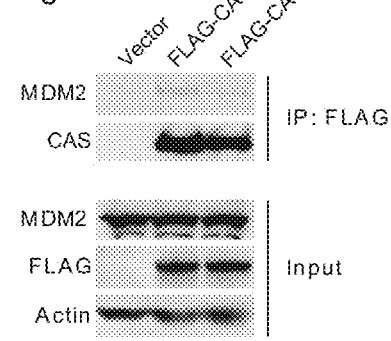
FIG. 11E is an immunoblot for FLAG-tagged proteins retrieved by immunoprecipitation and association with MDM2. H1299 cells were transfected with empty vector, FLAG-CAS$^{W127A}$, or FLAG-CAS wild type.
Figure 12A:
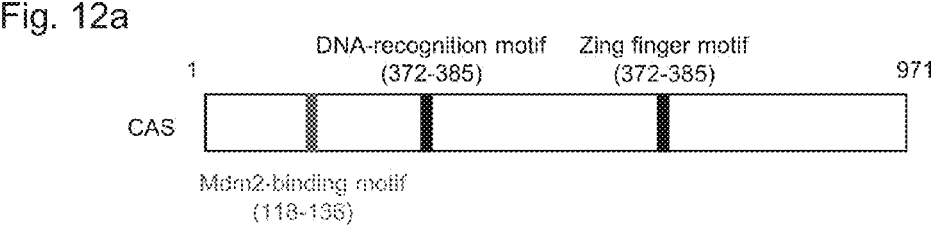
FIG. 12A is a schematic diagram of CAS/CSE1L protein sequence. The MDM2 binding motif is highlighted.

To determine the mode of CAS degradation, we analyzed the CAS protein sequence and identified a potential binding motif for the RING-finger ubiquitin ligase MDM2 (FIG. 12A and Table 2). Kussie, et al. *Science* 274, 948-953 (1996) and Uesugi & Verdine *Proc. Natl. Acad. Sci. USA* 96, 14801-14806 (1999). MDM2 co-immunoprecipitated with CAS in BT474 and HeLa cells. In addition to MDM2, CAS has also been shown to interact with p53. Tanaka, Ohkubo, Tatsuno & Prives. *Cell* 130, 638-650 (2007). However, the co-immunoprecipitation of MDM2 and CAS in p53-null H1299 cells suggests direct binding of the two proteins, an interaction that was enhanced in the presence of MG 132. Importantly, when Trp 127, a conserved residue in the MDM2 binding motif, was replaced with Ala, binding of CAS to MDM2 was diminished (FIG. 11E).

TABLE 2

| Protein (Source) | Start | Sequence | End | SEQ ID NO. |
|---|---|---|---|---|
| p53 (Homo sapiens): | 14 | LSQETFSDLW KLLPENNVL | 32 | 1 |
| p73 (Homo sapiens): | 10 | DGGTTFEHLW SSLEPDSTY | 28 | 2 |
| p63 (Homo sapiens): | 50 | LSPEVFQHIW DFLEQPICS | 68 | 3 |
| CAS/CSE1L (Homo sapiens): | 118 | IGREDFPQKW PDLLTEMVN | 136 | 4 |
| CSE1 (D. melanogaster): | 121 | IGKYDFPKKW PQLIDEMVE | 139 | 5 |
| CSE1 (S. cerevisiae): | 112 | IADSDFPDRW PTLLSDLAS | 130 | 6 |

The sequence alignment is shown that includes p53, p73, p63, CAS (*H. sapiens*), and CAS homologs (CSE1) from *D. melanogaster* and *S. cerevisiae* (bottom).

Figure 11F:
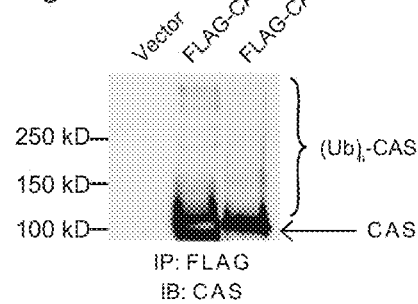
FIG. 11F is an immunoblot for CAs after immunoprecipitation for FLAG. H1299 cells were transfected with empty vector, FLAG-CAS$^{W127A}$, or FLAG-CAS wild type. Cells were treated with 10 µM MG132 for 3 hours.
Figure 11G:
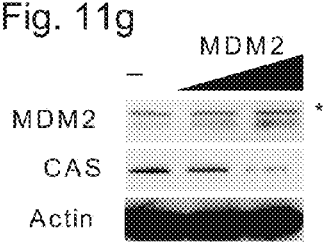
FIG. 11G is a set of immunoblots for MDM2, CAS and actin. SKBR3 cells were transfected with increasing amounts of MDM2. After 48 hours, cells were harvested and immunoblotted (*non-specific band).
Figure 11H:
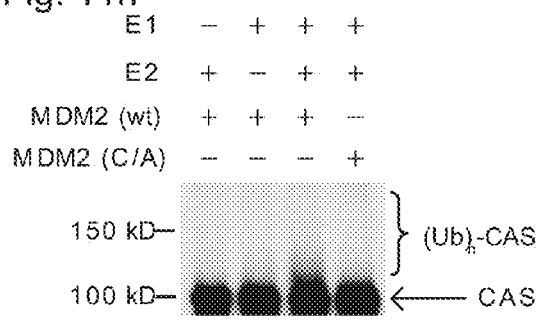
FIG. 11H is an immunoblot for CAS. Ubiquitylation of CAS was reconstituted in vitro by incubating recombinant CAS protein with E1, UbcH5 (E2), ubiquitin (Ub), and recombinant MDM2 protein (wild type (wt) or a catalytically inactive mutant (C/A)) in reaction buffer incubated at 37° C. for 3 hours and analyzed by immunoblotting for CAS.
Figure 11I:
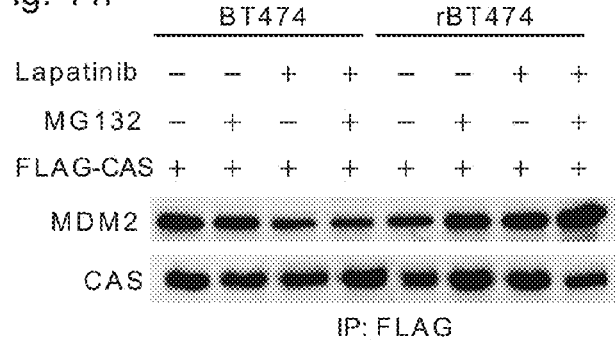
FIG. 11I is an immunoblot for MDM2 or CAs after immunoprecipitation with FLAG. BT474 and rBT474 cells were transfected with FLAG-CAS. Cells were treated with 1 µM lapatinib for 24 hours in the presence of z-VAD. After treatment with 10 µM MG132 for 5 hours, FLAG-CAS was retrieved by immunoprecipitation and association of endogenous MDM2 was analyzed by immunoblotting.

Moreover, when expressed in H1299 cells, ubiquitylation of CAS with the W127A mutation ($CAS^{W127A}$) was significantly suppressed compared with that of wild type CAS (FIG. 11F). Transient overexpression of MDM2 decreased endogenous CAS protein (FIG. 11G). Finally, recombinant MDM2, but not its Ring-finger domain mutant ($MDM2^{C464A}$), promoted in vitro ubiquitylation of CAS (FIG. 11H). Together, these results indicate that CAS is an MDM2 target. Interestingly, in BT474 cells, the CAS-MDM2 interaction decreased in the presence of lapatinib, whereas binding was enhanced in rBT474 cells under the same conditions (FIG. 11I). These data are consistent with the idea that augmented ubiquitylation and subsequent degradation of CAS protein in lapatinib-resistant cells is mediated by MDM2.

MDM2 is a Huwe1-Directed E3 Ligase

Figure 13A:
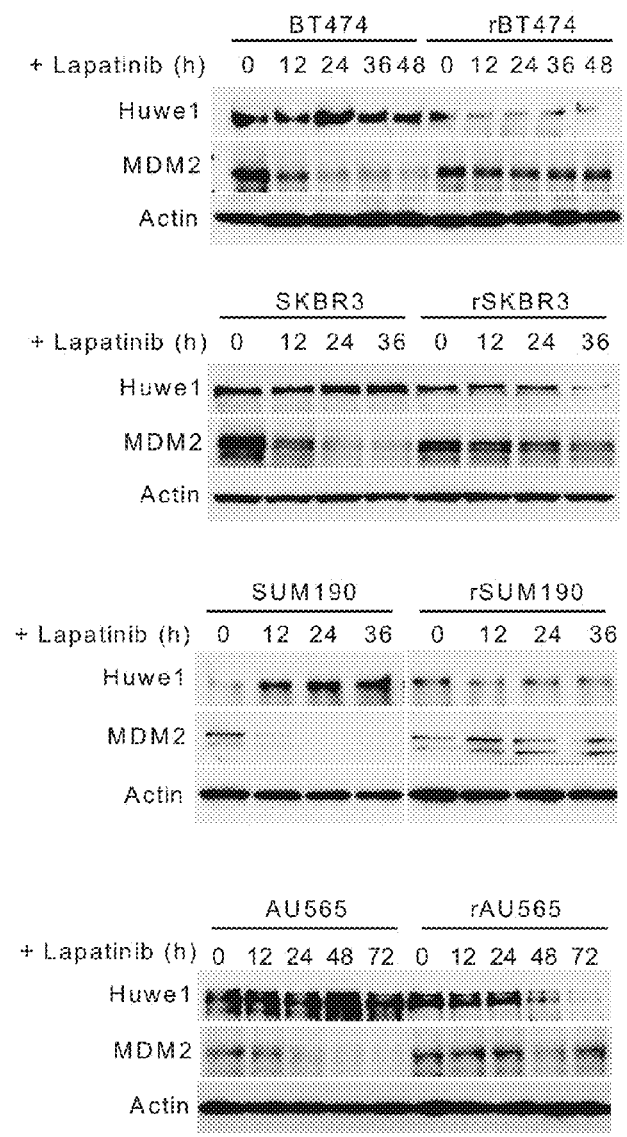
FIG. 13A is a set of immunoblots for Huwe1, MDM2, and Actin. Cells treated with 1 µM lapatinib were harvested at various time points and immunoblotted. MDM2 shows greater stability in the resistant cell lines in the presence of lapatinib.
Figure 13B:
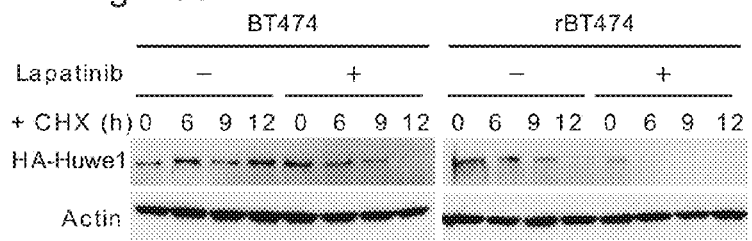
FIG. 13B is an immunoblot for HA and actin. BT474 and rBT474 cells were transiently transfected with HA-tagged Huwe1 and subsequently treated with 50 µg/ml cycloheximide (CHX) and 1 µM lapatinib.

High Huwe1 and low MDM2 activities in sensitive cells resulted in reduction of Mcl-1 and PP5 and sustained CAS levels, respectively, rendering the sensitive cells prone to apoptosis. In parental cells, Huwe1 protein levels remained stable in the presence of lapatinib, whereas MDM2 rapidly decreased (FIG. 13A). Conversely, when resistant cells were treated with lapatinib, Huwe1 levels significantly decreased, whereas MDM2 levels were maintained (FIG. 13A). Most importantly, reduction of Huwe1 in resistant cells appeared to be due to lapatinib-induced protein degradation. As shown in FIG. 13B, without lapatinib, Huwe1 was stable in both BT474 and rBT474 cells. However, in lapatinib-treated rBT474 cells, Huwe1 protein half-life became significantly shorter, compared to that in BT474 cells (FIG. 13B). Although both Huwe1 and MDM2 are p53-targeting E3 ligases (and MDM2 expression can also be modulated in a feedback loop by p53-induced transcription), three of the four cell lines (BT474, SKBR3, and SUM190) express mutant p53 (Table 1 and FIG. 1), suggesting that the observed changes in Huwe1 and MDM2 protein levels are independent of the transcriptional activity of p53.

Figure 12B:
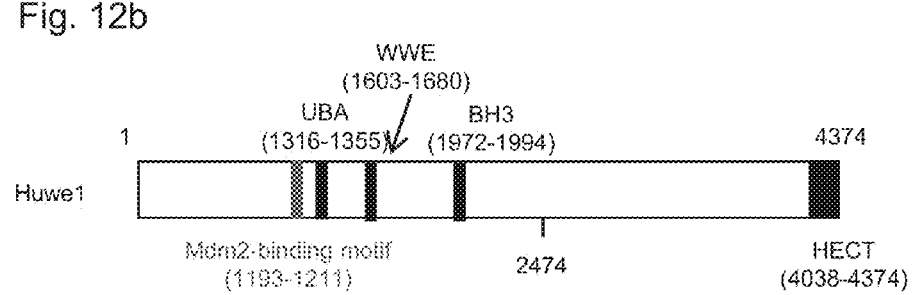
FIG. 12B is a schematic diagram of Huwe1 protein showing the MDM2 binding region.
Figure 13C:
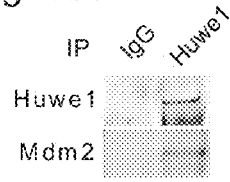
FIG. 13C is an immunoblot for Huwe1 and MDM2. Immunoprecipitation was carried out using H1299 cell lysates and anti-Huwe1 antibody (or control IgG).
Figure 13D:
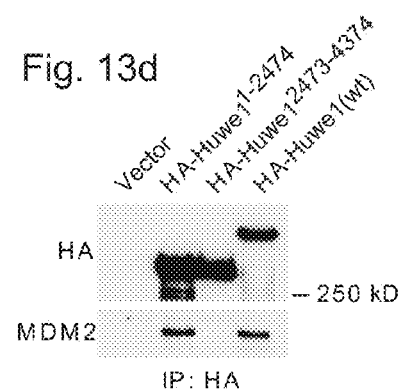
FIG. 13D is an immunoblot for HA or MDM2 after immunoprecipitation with HA. BT474 cells were transfected with HA-tagged Huwe1 encoding the full-length protein, residues 1-2474, or residues 2473-4374.
Figure 13E:
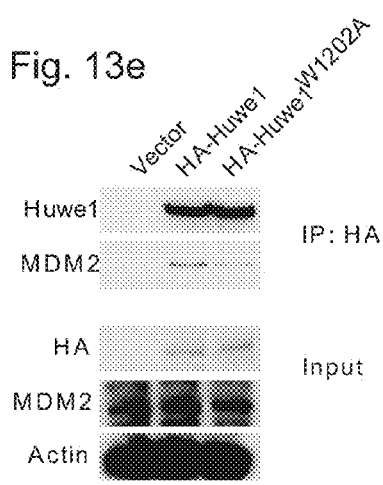
FIG. 13E is a set of immunoblots for Huwe1 or MDM2 after immunoprecipitation with HA. H1299 cells were transfected with empty vector, HA-Huwe1$^{W1202A}$, or HA-Huwe1 wild type.
Figure 13F:
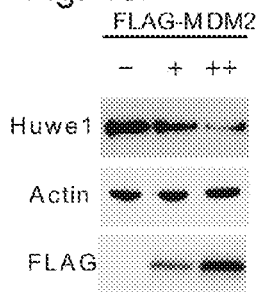
FIG. 13F is an immunoblot for Huwe1 and Actin. BT474 cells were transfected with increasing amounts of MDM2 and harvested after 48 hours.
Figure 13G:
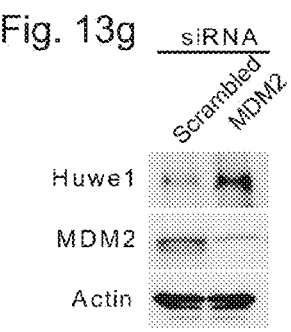
FIG. 13G is an immunoblot for Huwe1, MDM2, and actin. SUM190 cells were transfected with Scrambled or MDM2-specific siRNA (100 nM) and harvested after 72 hours.
Figure 13H:
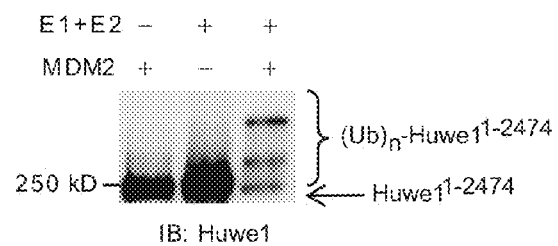
FIG. 13H is an immunoblot for Huwe1. Ubiquitylation of Huwe1 was reconstituted in vitro by incubating recombinant Huwe1 protein (Huwe1$^{1-2474}$) with E1, UbcH5 (E2), ubiquitin (Ub), and recombinant MDM2 protein in reaction buffer at 37° C. for 3 hours.
Figure 13I:
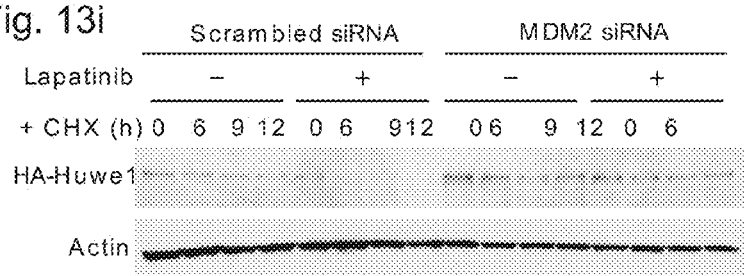
FIG. 13I is a set of immunoblots for HA and actin. rBT474 cells were transfected with scrambled or MDM2-specific siRNA (50 nM). Twenty-four hours later, the cells were replated and further transfected with HA-tagged Huwe1 (wild type). Forty-eight hours after siRNA transfection, the cells were treated with 1 µM lapatinib. After 24 hours of lapatinib treatment, 50 µg/ml cycloheximide (CHX) was added to the culture medium and cells were harvested at various time points for immunoblotting.

Through protein sequence analysis, we determined that Huwe1 contained a putative MDM2-binding motif at residues 1198-1205 (FIG. 12B and Table 3); the interaction of these two E3 ligases was confirmed by immunoprecipitation of endogenous proteins (FIG. 13C). The N-terminal portion of Huwe1 protein (aa1-2474) as well as the full-length protein interacted with MDM2 (FIG. 13D). Moreover, replacement of the conserved Trp1202 with Ala (Huwe1$^{W1202A}$) significantly reduced binding between the two proteins (FIG. 13E). Importantly, the Huwe1-MDM2 interaction was also evident in HeLa cells and H1299 cells, again indicating that their binding is neither specific for breast cancer cells nor mediated by p53. To determine whether MDM2 is a Huwe1-directed E3 ligase, we overexpressed MDM2 in H1299 cells. As shown in FIG. 13F, MDM2 expression reduced Huwe1 protein levels in a dose-dependent manner. In contrast, siRNA knockdown of MDM2 increased Huwe1 protein levels (FIG. 13G). Using a truncated mutant of Huwe1 (Huwe1$^{1-2474}$), to allow visualization of an electrophoretic mobility shift, we confirmed that, in the presence of both E1 and E2, MDM2 could ubiquitylate Huwe1 in vitro (FIG. 13H). Moreover, lapatinib treatment triggered degradation of Huwe1 in resistant cells treated with control siRNA, but when these cells were treated with MDM2 siRNA, Huwe1 stability was markedly increased, even in the presence of lapatinib, consistent with MDM2 acting as a Huwe1-directed ligase (FIG. 13I).

TABLE 3

| Protein (Source) | Start | Sequence | End | SEQ ID NO. |
|---|---|---|---|---|
| p53 (Homo sapiens): | 14 | LSQETFSDLW KLLPENNVL | 32 | 1 |
| Huwe1 (Homo sapiens): | 1193 | DGTGEFLDAW LMLVEKMVN | 1211 | 7 |
| (Mus musculus): | 1193 | DGTGEFLDAW LMLVEKMVN | 1211 | 8 |
| (Bos taurus): | 1193 | DGTGEFLDAW LMLVEKMVN | 1211 | 9 |
| (Danio rerio): | 1191 | DGTGEFLDAW LMLVEKMVN | 1209 | 10 |
| (Tribolium castaneum): | 1184 | EGTAGFLDAW LMLLEKMVN | 1202 | 11 |
| TOM1 (S. cerevisiae): | 1086 | DESN-----G ILTLSCLIN | 1099 | 12 |

The sequence alignment includes human p53, Huwe1 homologs from *H. sapiens, M. musculus, B. taurus, D. rerio, T. castaneum*, and TOM1 from *S. cerevisiae*.

Inhibition of MDM2 can Reverse Lapatinib Resistance

Figure 14A:
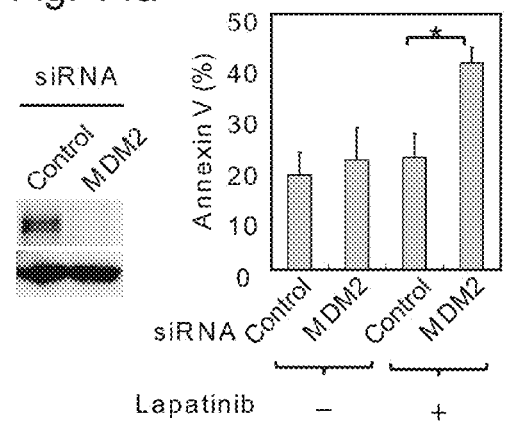
FIG. 14A is an immunoblot and associated graph. The immunoblot shows that the siRNA treatment was effective and the graph shows the MDM2 inhibitor can increase apoptosis in response to treatment with lapatinib. rBT474 cells were transfected with scrambled or MDM2-specific siRNA (20 nM). Forty-eight hours after siRNA transfection, cells were treated with 1 µM lapatinib for 48 hours, and cells were harvested and subjected to Annexin V staining. The percentage of Annexin V-positive cells was analyzed by FACS. Results are expressed as a mean percentage±SEM and analyzed by t-test (*P<0.05).
Figure 14B:
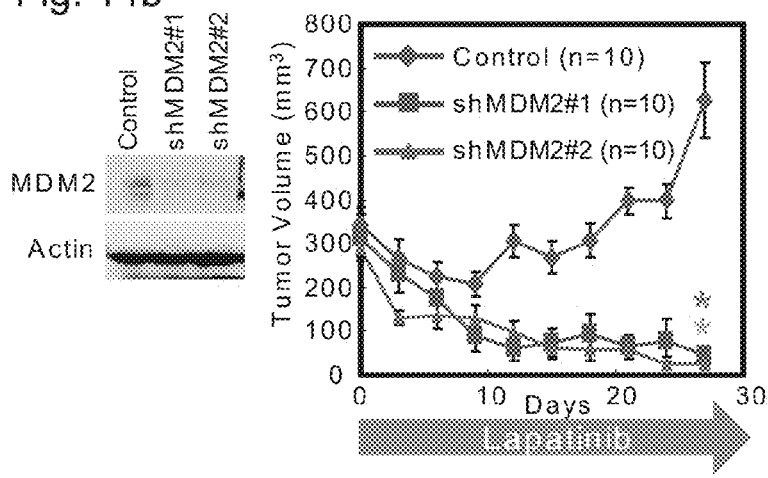
FIG. 14B is an immunoblot showing reduction in MDM2 by the shRNAs and a graph showing the effectiveness of shRNA targeting MDM2 to reduce tumor volume in a mouse. rBT474 cells stably expressing control or MDM2-specific shRNA (#1 or #2) were injected into the mammary fat pad of female nude mice. The oral administration of lapatinib (100 mg/kg, twice daily by oral gavage) began when the average tumor volume surpassed 300 mm$^3$. Results are expressed as a mean percentage±SEM. The statistical difference in tumor volume was analyzed by one-way ANOVA (P=0.000) followed by pairwise comparisons using the Bonferroni correction for multiple comparisons. *P<0.05 between control and shMDM2#1, and between control and shMDM2#2.

The findings above raised the interesting possibility that the observed changes in Mcl-1, PP5, and CAS in lapatinib-resistant cells could all be traced to high MDM2 activity in the resistant cells. Accordingly, when resistant cells were co-treated with lapatinib, MDM2 knockdown induced significant apoptotic cell death (FIG. 14A). To evaluate this further, we implanted xenografts of rBT474 cells stably expressing control or MDM2 shRNAs into the mammary fat pads of female nude mice (FIG. 14B). Tumors developed similarly for all tumors. Nevertheless, oral lapatinib administration induced regression of xenografted tumors expressing MDM2 shRNAs, while control tumors continued to grow (FIG. 14B). Moreover, by the end of treatment period, six out of ten mice in the MDM2 knock-down group had tumors smaller than 50 mm$^3$.

Figure 14C:
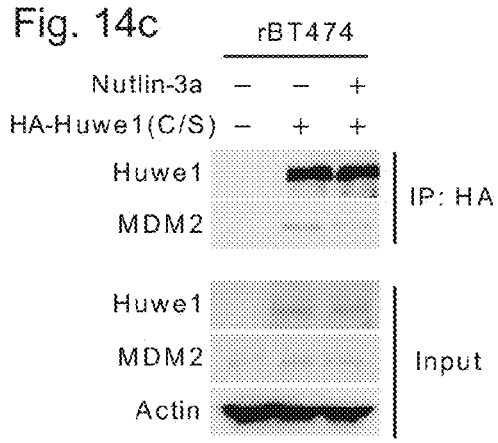
FIG. 14C is a set of immunoblots for MDM2, Huwe1 and actin. H1299 cells were transfected with HA-Huwe1 (C/S). Twenty-four hours post-transfection, cells were treated with 10 µM Nutlin-3a for 6 hours. HA-Huwe1 (C/S) was retrieved by immunoprecipitation and association of MDM2 was analyzed by immunoblotting.
Figure 14D:
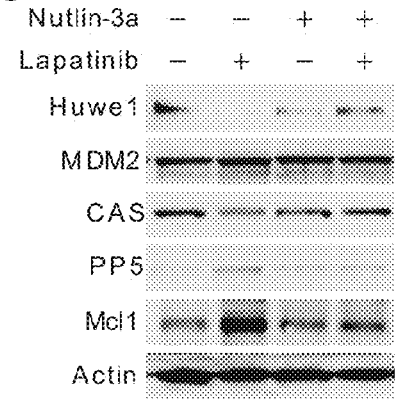
FIG. 14D is a set of immunoblots for Huwe1, CAS, MDM2, PP5, Mcl-1, and Actin. rSKBR3 cells were cultured in the presence or absence of 1 µM lapatinib for a week, and then treated with 10 µM Nutlin-3a in the presence of z-VAD. After 36 hours, cells were harvested and immunoblotted.

A hydrophobic pocket in the MDM2 N-terminus binds the transactivation domain of p53. If MDM2 bound Huwe1 in the same fashion, the MDM2 antagonist Nutlin-3a, that disrupts the p53-MDM2 complex, might also be expected to interfere with Huwe1-MDM2 binding. Vassilev, et al. *Science* 303, 844-848 (2004). To exclude the possibility that any effects of Nutlin-3a might be mediated by the p53-MDM2 interaction, we employed H1299 cells. Catalytically inactive Huwe1 (Huwe1(C/S)) bound to endogenous MDM2 and this binding was significantly reduced by Nutlin-3a (FIG. 14C). Importantly, Nutlin-3a also prevented lapatinib-induced degradation of Huwe1 (FIG. 14D), suggesting that Nutlin-3a stabilizes Huwe1 by disrupting Huwe1-MDM2 binding. Consequently, Nutlin-3a also suppressed lapatinib-induced upregulation of Mcl-1 and PP5 (FIG. 14D). MDM2 and CAS binding, as well as CAS degradation, was also significantly inhibited by Nutlin-3a (FIG. 14D).

Figure 14E:
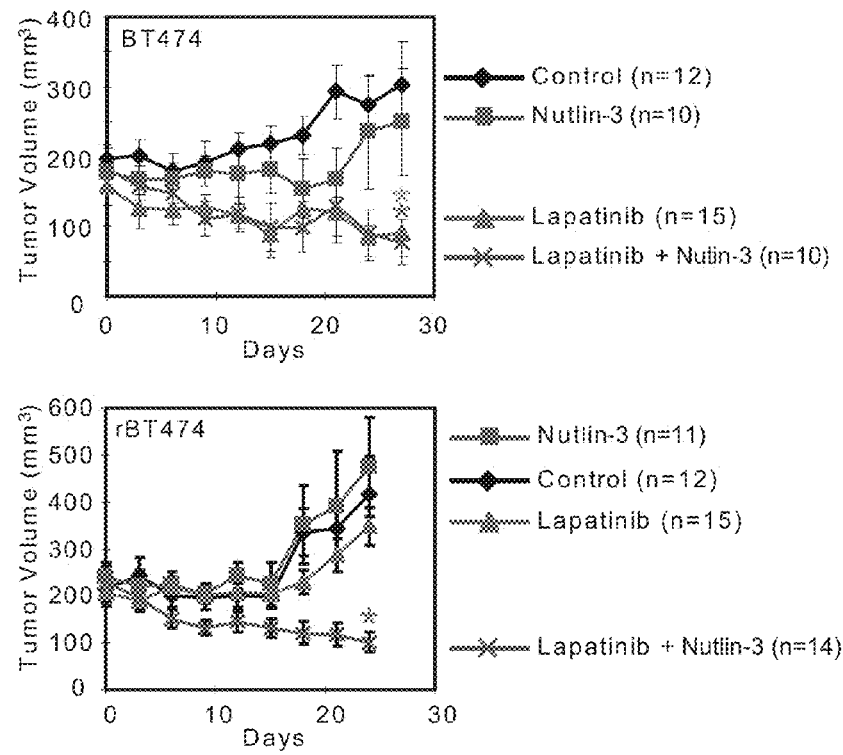
FIG. 14E is a set of graphs comparing the effectiveness of treatment with an MDM2 inhibitor, nutlin-3a, alone or in combination with lapatinib to treat a tumor in a mouse. BT474 and rBT474 cells were injected into the mammary fad pad of each mouse. When tumors developed to a size of 200 mm$^3$, the mice were randomly assigned to receive vehicle, lapatinib (100 mg/kg), Nutlin-3 (100 mg/kg), or Lapatinib+Nutlin-3 and treated twice daily by oral gavage. Results are expressed as a mean percentage±SEM. The statistical difference in tumor volume was analyzed by one-way ANOVA (P=0.003 and P=0.000 for BT474 and rBT474 xenografts. respectively) followed by pairwise comparisons using the Bonferroni correction for multiple comparisons. (Top) *P<0.05 between control and lapatinib, and between control and lapatinib+Nutlin-3, whereas the difference was not significant between control and Nutlin-3 in BT474 xenografts. (Bottom) *P<0.05 between control and lapatinib+Nutlin-3 whereas there was no significant difference between control and Nutlin-3, and between control and lapatinib in rBT474 xenografts.
Figure 14F:
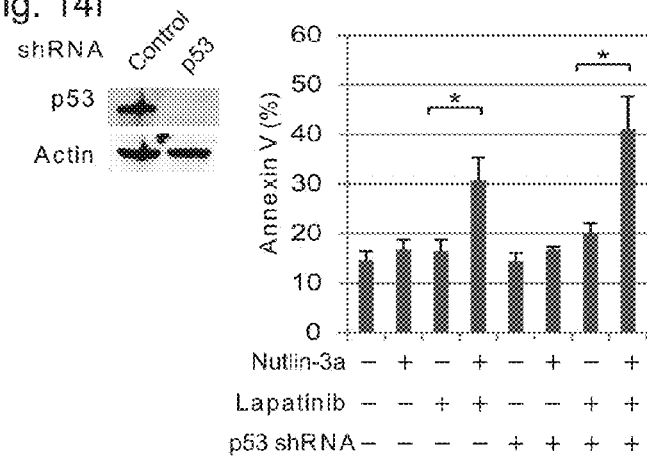
FIG. 14F is an immunoblot showing that the shRNA targeting p53 is effective and a graph showing the results of a FACS analysis for Annexin V. rAUS65 cells stably expressing control or p53-specific shRNA were treated with DMSO or 10 µM Nutlin-3a in the presence of absence of 1 µM lapatinib for 48 hours. Percentage of apoptotic cell death was measured by FACS analysis using Annexin V. Results are expressed as a mean percentage±SEM of Annexin V-positive cells (*P<0.05 by t-test).
Figure 14G:
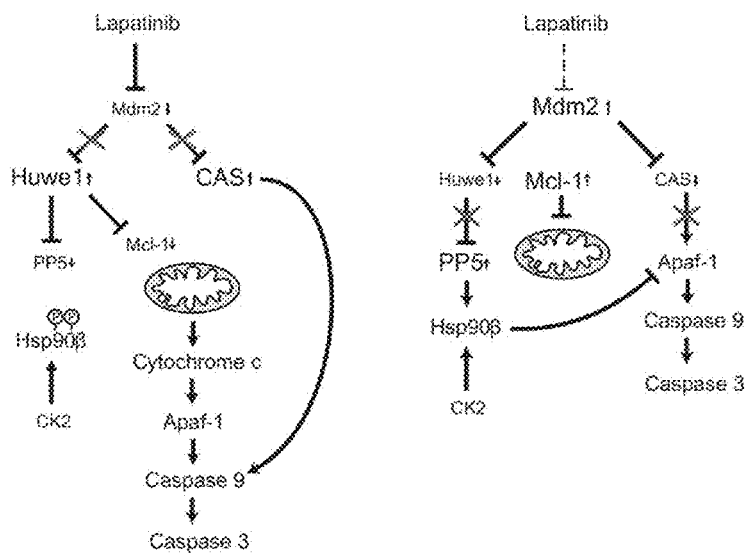
FIG. 14G is a model for coordinate control of multiple apoptotic regulators by the MDM2 and Huwe1. In sensitive cells, lapatinib promotes MDM2 degradation, which leads to elevations in Huwe1. This results in more PP5 and Mcl-1 degradation (loss of MDM2 also leads to less CAS degradation). In lapatinib-resistant cells, MDM2 promotes decreased CAS levels, decreased Huwe1 levels and consequently increased PP5 and Mcl-1. In aggregate, these changes render the cells resistant to lapatinib-induced apoptosis.
Figure 15:
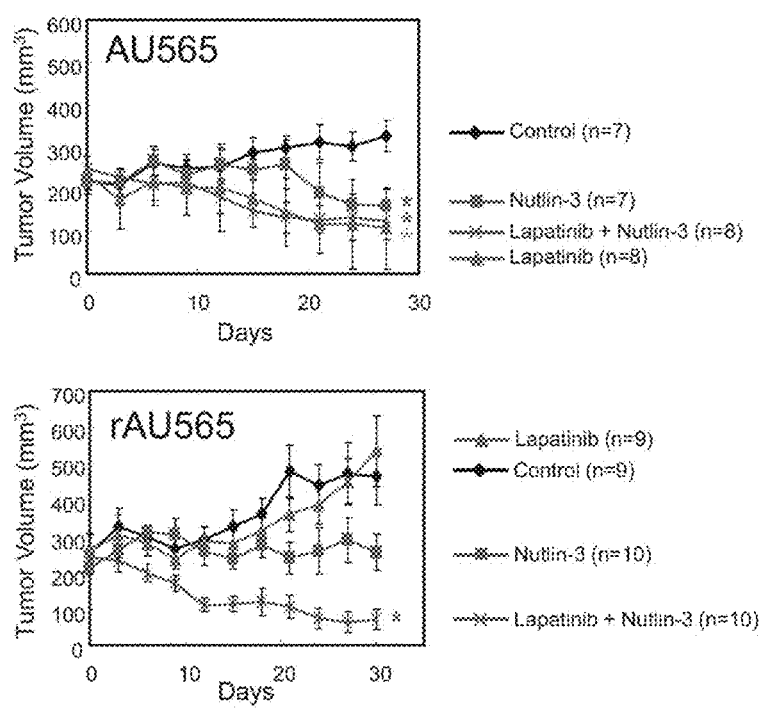
FIG. 15 is a set of graphs similar to those presented above in FIG. 14E but using AU565 and rAU565 as the cells. (Top) *P<0.05 between control and lapatinib, between control and Nutlin-3 and between control and lapatinib+Nutlin-3. (Bottom) *P<0.05 between control and lapatinib+Nutlin-3 whereas there was no significant difference between control and Nutlin-3, and between control and lapatinib.

To examine the effect of Nutlin-3a in vivo, mice bearing BT474 or rBT474 xenografts were randomly assigned to vehicle, lapatinib, Nutlin-3 (a racemic mixture of the enantiomers Nutlin-3a and Nutlin-3b), or lapatinib and Nutlin-3. Lapatinib alone or a combination of lapatinib and Nutlin-3 significantly suppressed growth of BT474-derived tumors, whereas Nutlin-3 alone only modestly inhibited tumor growth (FIG. 14E). Neither lapatinib nor Nutlin-3 inhibited rBT474-derived tumor growth as a single agent (FIG. 14E). Nevertheless, combination treatment of lapatinib and Nutlin-3 significantly suppressed tumor growth, resulting in ~50% reduction in tumor volume (FIG. 14E). These experiments were repeated using p53-positive AU565 and rAU565 cells. Lapatinib substantially inhibited AU565, but not rAU565-derived tumor growth (FIG. 15). Nutlin-3 treatment alone had moderate tumor inhibitory effects on these p53-positive cells, but combination lapatinib/nutlin-3 treatment reduced tumor volume by ~50% by the end of evaluation period (FIG. 15). Tissue culture experiments conducted in parallel with all four sensitive/resistant cell line pairs using the MDM2 antagonist MI-219, suggest that similar effects are likely to be obtained with other MDM2 inhibitors (FIG. 2). Importantly, the ability of the MDM2 inhibitors to re-sensitize resistant cells to lapatinib was not compromised by RNAi-mediated knock-down of p53 in rAU565 cells (FIG. 14F). Taken together, these results demonstrate that regardless of p53 status, an MDM2 inhibitor, such as Nutlin-3a, can reverse lapatinib resistance, potentially by stabilizing CAS and Huwe1, thereby promoting loss of PP5 and Mcl-1 (FIG. 14G).

We have demonstrated that multiple changes in the levels of apoptotic regulators, both upstream and downstream of mitochondrial cytochrome c release, cause resistance to lapatinib. Furthermore, these changes could be attributed to a previously unsuspected network of MDM2 (and Huwe1) substrates. Failure to degrade MDM2 in response to lapatinib in all four independently-derived lapatinib-resistant cell lines was the key factor in upregulating the anti-apoptotic machinery in these cells (see Model, FIG. 14G).

We identified changes in mitochondrial cytochrome c release following lapatinib treatment, but also have found that the apoptosome is refractory to cytochrome c-induced activation in the resistant cells. There is some debate as to the significance of apoptosome inhibition in cancers which already have a block to mitochondrial cytochrome c release. However, we postulate that the block is more profound when several loci in the apoptotic pathway are affected: even if small amounts of cytochrome c were released in response to lapatinib in the resistant cells, efficient caspase activation would be inhibited at the level of the apoptosome. Since PP5 and Mcl-1 are both controlled by Huwe1, apoptotic inhibition both upstream and downstream of the mitochondria could be controlled coordinately.

We also determined that CAS was downregulated through MDM2-mediated ubiquitylation. Interestingly, CAS was identified as a gene which, when knocked down, renders breast cancer cells resistant to apoptosis. CAS also binds to a subset of p53 target genes to regulate p53-mediated gene expression. In this regard, our results raise the interesting possibility that, in addition to ubiquitylation of p53, MDM2 might also modulate the p53 signaling pathway by targeting CAS for degradation. Alteration of multiple apoptotic regulators in lapatinib-resistant cells also increased their resistance to other pro-apoptotic stimuli (e.g. other potential therapeutics such as taxol and other apoptotic inducers such as staurospaurine) in the presence of lapatinib. These data raise the significant concern that modulation of apoptotic pathways in lapatinib-resistant cells might confer cross-resistance to multiple chemotherapeutic agents.

Figure 16:
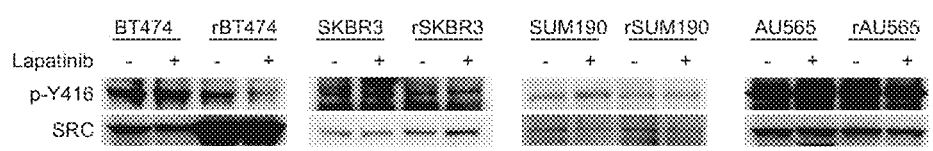
FIG. 16 is a set of immunoblots for total SRC and phosphor-SRC (Y416) in the cell lines used in this study. Cells were treated with DMSO or lapatinib (1 µM) for 24 hours in the presence of caspase inhibitor z-VAD.
Figure 17:
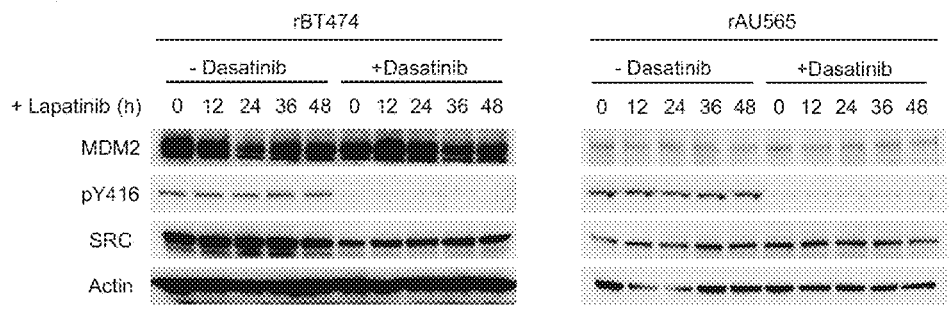
FIG. 17 is a set of immunoblots for MDM2, pY416, SRC and actin in two of the resistant cell lines after pre-treatment with DMSO or 1 µM dasatinib for 24 hours followed by treatment of the cells with 1 µM lapatinib and harvested at the indicated time points.

The basis for the difference in MDM2 levels in resistant and sensitive cells is not clear. In BT474/rBT474 cells, we have seen marked differences in MDM2 half-life as well as changes in MDM2 RNA levels. Note that we did not detect consistent upregulation of SRC kinase activity (FIG. 16), recently implicated in acquired resistance to trastuzumab or lapatinib in HER2(+) breast cancer. Zhang, et al. *Nat. Med.* 17, 461-469 (2011) and Rexer et al. *Oncogene* 30(40):4163-74 (2011). The SRC inhibitor dasatinib also did not affect MDM2 protein levels or apoptotic resistance in lapatinib-resistant cells (FIG. 17). It is possible that a mutation, modification, or novel binding partner renders MDM2 unable to auto-ubiquitylate, but still able to ubiquitylate substrates in trans. Finally, failure to degrade MDM2 in the resistant cells could result from mutation in MDM2 itself, rendering it insensitive to degradative signals triggered by lapatinib in sensitive cells. Answering these questions will provide a stepping-stone from MDM2 to the relevant signaling factor(s) primarily responsible for the lapatinib resistance, while revealing additional nodes in the MDM2/Huwe1 regulatory network.

METHODS

Cell Culture

BT474, SKBR3, and AU565 cells were obtained from ATCC. SUM190 cells were obtained from Asterand, Inc. All cell lines were cultured in RPMI medium containing 10% fetal bovine serum (FBS). Lapatinib-resistant cells (rBT474, rSKBR3, rAU565, and rSUM190) were established as previously described[14]. Cobleigh, et al. *J. Clin. Oncol.* 17, 2639-2648 (1999). Lapatinib-resistant cells were grown in the presence of 1 µM lapatinib unless otherwise stated.

Reagents and Antibodies

Lapatinib and dasatinib were purchased from LC Laboratories. MG132 and z-VAD were purchased from Enzo Life Sciences. E1, E2, ubiquitin, and Ub-Aldehyde were purchased from Boston Biochem. Nutlin-3a and racemate Nutlin-3 were synthesized and purified at the Duke Small Molecule Synthesis Facility. Nutlin-3a and Nutlin-3 were also purchased from Cayman Chemical. Cycloheximide and purified cytochrome c was purchased from Sigma.

The following antibodies were used: anti-HER2 antibody, anti-phospho-HER2 (Y877) antibody, anti-phospho-HER2 (Y1221/Y1222) antibody, anti-Akt antibody, anti-phospho-Akt (T308) antibody, anti-caspase-9 antibody, anti-cleaved caspase-3 antibody, anti-Bcl2 antibody, anti-Bcl-xL antibody, anti-ERK1/2 antibody, anti-phospho-ERK1/2 antibody (T202/Y204), anti-phospho-SRC (Y416) antibody, anti-SRC antibody, anti-FLAG antibody (Cell Signaling), anti-Apaf-1 antibody (2E12: Enzo Life Sceinces), anti-HSP90β antibody (5E12), anti-MDM2 antibody (2A10: Calbiochem), anti-HSP90β antibody (Millipore), anti-phospho-HSP90β antibody (S226), anti-phospho-HSP90β antibody (S255) (Abcam), anti-Actin antibody, anti-MDM2 antibody (SMP14), anti-HA antibody (F-7) (Santa Cruz Biotechnology), anti-FLAG M2 antibody (Sigma), anti-Bim antibody, anti-cleaved caspase-3 antibody, anti-Mcl-1 antibody, anti-PP5 antibody, anti-CAS antibody, anti-HSP70 antibody (BD Transduction Laboratories), anti-Mcl-1 antibody (BioLegend), anti-Huwe1 antibody (Bethyl Laboratories), anti-PHAP1 antibody (ProSci).

Plasmids

HA-Huwe1 constructs in pCMV (wild type, C4341S mutant, and as 2473-4374 mutant) were generous gifts from Kristian Helin (University of Copenhagen). Huwe1 in pENTR was generous gifts from Jeanette Gowen Cook (University of North Carolina, Chapel Hill). Huwe1 in pENTR was recombined with the destination vector pDEST10 (Invitrogen) for production of His-tagged protein. FLAG-PP5 in pcDNA3 and FLAG-CAS in p3XFLAG-CMV10 were kind gifts from Xiao-Fan Wang (Duke University) and Carol Prives (Columbia University), respectively. CAS was also cloned into pENTR and, subsequently, into pDEST10 for baculoviral protein expression. PP5 was cloned into pGEX-KG for production of GST fusion protein. Mcl-1 with the N-terminal FLAG tag was generated from human Mcl-1 (a gift from Jeffrey Rathmell, Duke University) and cloned into pcDNA3. The plasmids encoding GST-MDM2, GST-MDM2$^{C464A}$, and HA-ubiquitin were obtained from Addgene (Addgene plasmids 11492, 11493, and 17608). Fang, et al. *J. Biol. Chem.* 275, 8945-8951 (2000) and Lim. et al. *J. Neurosci.* 25, 2002-2009 (2005). MDM2 was also cloned into pcDNA3 with an N-terminal FLAG tag. All point mutations (HA-Huwe1$^{1-2474}$, HA-Huwe1$^{W1202A}$, His-Huwe1$^{C4341S}$, FLAG-CAS$^{W127A}$) were generated with the QuikChange mutagenesis kit (Stratagene).

RNAi

Transient siRNA transfections were performed using Lipofectamine RNAiMAX (Invitrogen) according to manufacturer's instruction. MDM2-specific siRNA (sense: 5'-CACCUCACAGAUUCCAGCUUCGGAA-3'; SEQ ID NO: 13) and its scrambled siRNA control (sense: 5'-CACACACUUAGGACCCUUCGUCGAA-3'; SEQ ID NO: 14) were designed and synthesized by Invitrogen. siRNA oligos targeting Huwe1 or GFP were previously described. Hall et al. *Mol. Biol. Cell* 18, 3340-3350 (2007).

For stable knockdown of MDM2, an shRNA construct in the lentiviral vector pLKO.1-puro (shMDM2 #1) was purchased from Open Biosystems (sense: 5'-GATTCCAGAGAGTCATGTGTT-3'; SEQ ID NO: 15). An additional MDM2 shRNA construct (shMDM2 #2 sense: 5'-TTGAAGTTATTAAAGTCTGTT-3'; SEQ ID NO: 16) and control shRNA construct (sense: 5'-CTGTGCTGTAGGTGAAACTGT-3'; SEQ ID NO: 17) were also created in the vector pLKO.1-puro according to Addgene's pLKO.1 protocol (http://www.addgene.org/plko). Stable knockdown of p53 was performed using the vector shp53-pLKO.1-puro (Addgene plasmid 19119). Godar et al. *Cell* 134, 62-73 (2008).

Mouse Xenograft Experiments

Six week-old female nude mice were purchased from NCI Frederic. Xenograft tumors were produced by injection into the mammary fat pad with cells ($10 \times 10^6$). Tumor volumes were calculated every 3-4 days based on caliper measurements of the short (a) and long (b) tumor diameters (volume=$a^2b/2$). Lapatinib and Nutlin-3 were formulated in vehicle (water with 0.5% Hydroxypropyl methylcellulose and 0.1% Tween). Mice were dosed orally with vehicle alone, lapatinib (100 mg/kg), Nutlin-3 (100 mg/kg), or combination of both twice daily by gavage.

Immunoprecipitation

Cells were transiently transfected with the indicated plasmid by FuGene6 (Roche) based on manufacturer's instruction. Cells were harvested and lysed with co-IP buffer (10 mM HEPES [pH 7.4], 150 mM KCl, 0.5% NP-40, 1 mM phenylmethylsulfonyl fluoride, 5 µg/ml leupeptin, and 5 µg/ml aprotinin). Cell lysate was incubated with anti-FLAG M2 agarose (Sigma) or anti-AH affinity matrix (Roche) at 4° C. for 2-3 hours. The bead pellet was washed three times with co-IP buffer and then incubated with SDS-sample buffer.

Apoptosis Assays

Cell lysates for apoptotic assays were prepared as described previously using buffer A (20 mM HEPES [pH 7.4], 10 mM KCl, 1.5 mM MgCl2, 1 mM EDTA, 1 mM EGTA, 1 mM dithiothreitol, 1 mM phenylmethylsulfonyl fluoride, 5 µg/ml leupeptin, and 5 µg/ml aprotinin). Kurokawa, Zhao, Reya, & Kornbluth. *Mol. Cell. Biol.* 28, 5494-5506 (2008). Cell lysate (10 µg/µl) was incubated in the presence or absence of 1 mM dATP and various concentrations of cytochrome c at 37° C. for 30 min, and subjected to gel filtration, caspase assays, or western blotting.

Gel filtration was performed as previously described. Spector, Xia, El-Hariry, Yarden, & Bacus. *Breast Cancer Res.* 9, 205-212 (2007). After incubation with cytochrome c, the cell lysate (in a volume of 250 µl) was loaded onto a Superdex 200 column at a flow rate of 0.3 ml/min.

Colorimetric caspase assays were performed by incubating cell lysate (3 µl) in 90 µl DEVDase buffer (50 mM HEPES [pH 7.5], 100 mMNaCl, 0.1% CHAPS, 10 mMDTT, 1 mMEDTA, 10% glycerol) containing the peptide substrate, Ac-DEVD-pNA (200 mM final concentration; BIOMOL Research Labs). Reactions were incubated at 37° C. for 30 min. Absorbance of the colorimetric product was measured at 405 nm using a Bio-Rad microplate reader.

In Vitro Ubiquitylation Assays

Recombinant human PP5 and MDM2 proteins were bacterially expressed with a GST tag. After purification by glutathione sepharose 4B (GE Healthcare), the GST tag was cleaved off by thrombin. Recombinant human Huwe1 wild type, C4341S mutant (Huwe1 C/S), and Huwe1$^{1-2474}$ were expressed in the baculovirus system and purified from Sf9 cells.

For in vitro ubiquitylation assays, 100 ng of purified recombinant PP5 or Huwe1$^{1-2474}$ was incubated with 10 ng E1, 100 ng E2 (UbcH5b or UbcH7), 100 µg ubiquitin, and 0.5 µg of a purified E3 enzyme (Huwe1 wild type, Huwe1 C/S, or MDM2) in 40 µl of reaction buffer (50 mM Tris, pH 7.5, 5 mM MgCl$_2$, 2 mM ATP, 2 mM DTT). After incubation at 30° C. for 3 hours, the reaction was terminated by addition of SDS-sample buffer.

Statistics

The statistical analysis was carried out using GraphPad Prism software version 4.0c (GraphPad software Inc.).

We claim:

1. A method of developing a treatment plan for an individual with cancer comprising obtaining a sample comprising cancer cells from a subject; assaying the cells to determine the level of at least three of p53, MDM2, PP5, CAS or Huwe1 in the cancer cells as compared to the level in control cells and administering a MDM2 inhibitor to the subject if the cancer cells lack wild-type p53, have increased levels of MDM2 or PP5 or has decreased levels of CAS or Huwe1 as compared to control cells.

2. The method of claim 1, wherein the level of p53, MDM2, PP5, CAS and Huwe1 are all assayed.

3. The method of claim 1, further comprising administering a tyrosine kinase inhibitor.

4. The method of claim 3, wherein the tyrosine kinase inhibitor comprises an inhibitor of HER2, an inhibitor of EGFR, or both.

5. The method of claim 4, wherein the tyrosine kinase inhibitor comprises lapatinib.

6. The method of claim 1, wherein the level of at least four of p53, MDM2, PP5, CAS or Huwe1 is determined.

7. The method of claim 1, wherein the subject is a human.

8. The method of claim 1, wherein the cancer is breast cancer, lung cancer, colon cancer, gastric cancer or glioma.

9. The method of claim 1, wherein the inhibitor of MDM2 is nutlin-3 or nutlin-3a or is a spiro-oxindole.

10. A method comprising obtaining a sample comprising cancer cells from a subject; and assaying the cells to determine the level of at least three of p53, MDM2, PP5, CAS or Huwe1 in the cancer cells as compared to the level in control cells.

11. The method of claim 10, wherein the level of at least four of p53, MDM2, PP5, CAS or Huwe1 is determined.

12. The method of claim 10, wherein the level of p53, MDM2, PP5, CAS and Huwe1 are all assayed.

13. The method of claim 10, wherein the subject is a human.

14. The method of claim 10, wherein the cancer is breast cancer, lung cancer, colon cancer, gastric cancer or glioma.

* * * * *

SEQUENCE LISTING

<160> NUMBER OF SEQ ID NOS: 17

<210> SEQ ID NO 1
<211> LENGTH: 19
<212> TYPE: PRT
<213> ORGANISM: Homo sapiens
<220> FEATURE:
<221> NAME/KEY: misc_feature
<223> OTHER INFORMATION: P53 human

<400> SEQUENCE: 1

Leu Ser Gln Glu Thr Phe Ser Asp Leu Trp Lys Leu Leu Pro Glu Asn
1               5                   10                  15

Asn Val Leu

<210> SEQ ID NO 2
<211> LENGTH: 19
<212> TYPE: PRT
<213> ORGANISM: Homo sapiens

```
<220> FEATURE:
<221> NAME/KEY: misc_feature
<223> OTHER INFORMATION: P73 human

<400> SEQUENCE: 2

Asp Gly Gly Thr Thr Phe Glu His Leu Trp Ser Ser Leu Glu Pro Asp
1               5                   10                  15

Ser Thr Tyr

<210> SEQ ID NO 3
<211> LENGTH: 19
<212> TYPE: PRT
<213> ORGANISM: Homo sapiens
<220> FEATURE:
<221> NAME/KEY: misc_feature
<223> OTHER INFORMATION: P63 human

<400> SEQUENCE: 3

Leu Ser Pro Glu Val Phe Gln His Ile Trp Asp Phe Leu Glu Gln Pro
1               5                   10                  15

Ile Cys Ser

<210> SEQ ID NO 4
<211> LENGTH: 19
<212> TYPE: PRT
<213> ORGANISM: Homo sapiens
<220> FEATURE:
<221> NAME/KEY: misc_feature
<223> OTHER INFORMATION: CAS/CSE1L human

<400> SEQUENCE: 4

Ile Gly Arg Glu Asp Phe Pro Gln Lys Trp Pro Asp Leu Leu Thr Glu
1               5                   10                  15

Met Val Asn

<210> SEQ ID NO 5
<211> LENGTH: 19
<212> TYPE: PRT
<213> ORGANISM: D. melanogaster
<220> FEATURE:
<221> NAME/KEY: misc_feature
<223> OTHER INFORMATION: CSE1

<400> SEQUENCE: 5

Ile Gly Lys Tyr Asp Phe Pro Lys Lys Trp Pro Gln Leu Ile Asp Glu
1               5                   10                  15

Met Val Glu

<210> SEQ ID NO 6
<211> LENGTH: 19
<212> TYPE: PRT
<213> ORGANISM: S. cerevisiae
<220> FEATURE:
<221> NAME/KEY: misc_feature
<223> OTHER INFORMATION: CSE1

<400> SEQUENCE: 6

Ile Ala Asp Ser Asp Phe Pro Asp Arg Trp Pro Thr Leu Leu Ser Asp
1               5                   10                  15

Leu Ala Ser

<210> SEQ ID NO 7
<211> LENGTH: 19
<212> TYPE: PRT
```

<213> ORGANISM: Homo sapiens
<220> FEATURE:
<221> NAME/KEY: misc_feature
<223> OTHER INFORMATION: Huwe1

<400> SEQUENCE: 7

Asp Gly Thr Gly Glu Phe Leu Asp Ala Trp Leu Met Leu Val Glu Lys
1               5                   10                  15

Met Val Asn

<210> SEQ ID NO 8
<211> LENGTH: 19
<212> TYPE: PRT
<213> ORGANISM: Mus musculus
<220> FEATURE:
<221> NAME/KEY: misc_feature
<223> OTHER INFORMATION: Huwe1

<400> SEQUENCE: 8

Asp Gly Thr Gly Glu Phe Leu Asp Ala Trp Leu Met Leu Val Glu Lys
1               5                   10                  15

Met Val Asn

<210> SEQ ID NO 9
<211> LENGTH: 19
<212> TYPE: PRT
<213> ORGANISM: Bos taurus
<220> FEATURE:
<221> NAME/KEY: misc_feature
<223> OTHER INFORMATION: Huwe1

<400> SEQUENCE: 9

Asp Gly Thr Gly Glu Phe Leu Asp Ala Trp Leu Met Leu Val Glu Lys
1               5                   10                  15

Met Val Asn

<210> SEQ ID NO 10
<211> LENGTH: 19
<212> TYPE: PRT
<213> ORGANISM: Danio rerio
<220> FEATURE:
<221> NAME/KEY: misc_feature
<223> OTHER INFORMATION: Huwe1

<400> SEQUENCE: 10

Asp Gly Thr Gly Glu Phe Leu Asp Ala Trp Leu Met Leu Val Glu Lys
1               5                   10                  15

Met Val Asn

<210> SEQ ID NO 11
<211> LENGTH: 19
<212> TYPE: PRT
<213> ORGANISM: Tribolium castaneum
<220> FEATURE:
<221> NAME/KEY: misc_feature
<223> OTHER INFORMATION: Huwe1

<400> SEQUENCE: 11

Glu Gly Thr Ala Gly Phe Leu Asp Ala Trp Leu Met Leu Leu Glu Lys
1               5                   10                  15

Met Val Asn

<210> SEQ ID NO 12
<211> LENGTH: 14

```
<212> TYPE: PRT
<213> ORGANISM: S. cerevisiae
<220> FEATURE:
<221> NAME/KEY: misc_feature
<223> OTHER INFORMATION: TOM1

<400> SEQUENCE: 12

Asp Glu Ser Asn Gly Ile Leu Thr Leu Ser Cys Leu Ile Asn
1               5                   10

<210> SEQ ID NO 13
<211> LENGTH: 25
<212> TYPE: RNA
<213> ORGANISM: Artificial Sequence
<220> FEATURE:
<223> OTHER INFORMATION: Synthetic: MDM2-specific siRNA

<400> SEQUENCE: 13
caccucacag auuccagcuu cggaa                                      25

<210> SEQ ID NO 14
<211> LENGTH: 25
<212> TYPE: RNA
<213> ORGANISM: Artificial Sequence
<220> FEATURE:
<223> OTHER INFORMATION: Synthetic: MDM2-scrambled siRNA control

<400> SEQUENCE: 14
cacacacuua ggacccuucg ucgaa                                      25

<210> SEQ ID NO 15
<211> LENGTH: 21
<212> TYPE: DNA
<213> ORGANISM: Artificial Sequence
<220> FEATURE:
<223> OTHER INFORMATION: Synthetic: MDM2-specific shRNA number 1

<400> SEQUENCE: 15
gattccagag agtcatgtgt t                                          21

<210> SEQ ID NO 16
<211> LENGTH: 21
<212> TYPE: DNA
<213> ORGANISM: Artificial Sequence
<220> FEATURE:
<223> OTHER INFORMATION: Synthetic: MDM2-specific shRNA number 2

<400> SEQUENCE: 16
ttgaagttat taaagtctgt t                                          21

<210> SEQ ID NO 17
<211> LENGTH: 21
<212> TYPE: DNA
<213> ORGANISM: Artificial Sequence
<220> FEATURE:
<223> OTHER INFORMATION: Synthetic: MDM2 shRNA control

<400> SEQUENCE: 17
ctgtgctgta ggtgaaactg t                                          21
```